(12) United States Patent
Stad et al.

(10) Patent No.: US 8,414,588 B2
(45) Date of Patent: Apr. 9, 2013

(54) METHODS AND DEVICES FOR MINIMALLY INVASIVE SPINAL CONNECTION ELEMENT DELIVERY

(75) Inventors: Shawn Stad, Fall River, MA (US); Andrew Medeiros, Fall River, MA (US); Garth Baker, Somerset, MA (US); Paul Beaudoin, Derry, NH (US)

(73) Assignee: DePuy Spine, Inc., Raynham, MA (US)

( * ) Notice: Subject to any disclaimer, the term of this patent is extended or adjusted under 35 U.S.C. 154(b) by 457 days.

(21) Appl. No.: 12/244,268

(22) Filed: Oct. 2, 2008

(65) Prior Publication Data

US 2009/0143828 A1     Jun. 4, 2009

Related U.S. Application Data

(60) Provisional application No. 60/977,490, filed on Oct. 4, 2007.

(51) Int. Cl.
*A61B 17/70*     (2006.01)

(52) U.S. Cl.
USPC .......................... 606/86 A; 606/246; 606/279

(58) Field of Classification Search .......... 606/246–279, 606/86 A
See application file for complete search history.

(56) References Cited

U.S. PATENT DOCUMENTS

| | | | |
|---|---|---|---|
| 2,005,955 A | 6/1935 | Renouf |
| 2,248,054 A | 7/1941 | Becker |
| 2,268,576 A | 1/1942 | Drewett |
| 2,346,346 A | 4/1944 | Anderson |
| 2,514,589 A | 7/1950 | Penman |
| 2,684,168 A | 7/1954 | McGinnis |
| 3,224,799 A | 12/1965 | Blose |
| 3,997,138 A | 12/1976 | Crock |
| 4,041,636 A | 8/1977 | Folker |
| 4,274,401 A | 6/1981 | Miskew |
| 4,324,036 A | 4/1982 | Reilly |
| 4,369,011 A | 1/1983 | Ploss |

(Continued)

FOREIGN PATENT DOCUMENTS

| | | |
|---|---|---|
| DE | 2649042 | 9/1978 |
| DE | 2903342 | 7/1980 |

(Continued)

OTHER PUBLICATIONS

Moss Miami, Brochure "Polyaxial Reduction Screw", 1998 DePuy AcroMed, Inc.

(Continued)

*Primary Examiner* — Eduardo C Robert
*Assistant Examiner* — Nicholas Plionis

(57) ABSTRACT

A device for delivery of a spinal rod to a bone anchor includes an inner tube and an outer tube disposed about at least a portion of the inner tube. The inner tube is adjustable relative to the outer tube along the longitudinal axis of the outer tube between a first position and a second position in which the distal end of the inner tube contacts the bone anchor. A spring is interposed between the inner tube and the outer tube to bias the inner tube distally. A locking member is coupled to the outer tube and is adjustable between a proximal position in which the locking member is spaced apart from the inner tube and a distal position in which the locking member inhibits proximal axial motion of the inner tube relative to the outer tube.

16 Claims, 23 Drawing Sheets

U.S. PATENT DOCUMENTS

| | | |
|---|---|---|
| 4,373,754 A | 2/1983 | Bollfrass |
| 4,382,438 A | 5/1983 | Jacobs |
| 4,448,191 A | 5/1984 | Rodnyansky |
| 4,492,749 A | 1/1985 | Scheler |
| 4,611,580 A | 9/1986 | Wu |
| 4,763,644 A | 8/1988 | Webb |
| 4,799,372 A | 1/1989 | Marcon |
| 4,805,602 A | 2/1989 | Puno |
| 4,815,453 A | 3/1989 | Cotrel |
| 4,836,196 A | 6/1989 | Park |
| 4,848,368 A | 7/1989 | Kronner |
| 4,864,614 A | 9/1989 | Crowther |
| 4,887,596 A | 12/1989 | Sherman |
| 4,913,134 A | 4/1990 | Luque |
| 4,946,458 A | 8/1990 | Harms |
| 4,950,269 A | 8/1990 | Gaines, Jr. |
| 5,005,562 A | 4/1991 | Cotrel |
| 5,020,519 A | 6/1991 | Hayes |
| 5,042,982 A | 8/1991 | Harms |
| 5,052,643 A | 10/1991 | Law |
| 5,067,955 A | 11/1991 | Cotrel |
| 5,092,635 A | 3/1992 | DeLange |
| 5,092,867 A | 3/1992 | Harms |
| 5,092,893 A | 3/1992 | Smith |
| 5,129,388 A | 7/1992 | Vignaud |
| 5,154,719 A | 10/1992 | Cotrel |
| 5,171,279 A | 12/1992 | Mathews |
| 5,176,680 A | 1/1993 | Vignaud |
| 5,196,013 A | 3/1993 | Harms |
| 5,207,678 A | 5/1993 | Harms |
| 5,217,497 A | 6/1993 | Mehdian |
| 5,242,443 A | 9/1993 | Kambin |
| 5,242,446 A | 9/1993 | Steffee |
| 5,261,907 A | 11/1993 | Vignaud |
| 5,261,912 A | 11/1993 | Frigg |
| 5,261,913 A | 11/1993 | Marnay |
| 5,282,862 A | 2/1994 | Baker |
| 5,282,863 A | 2/1994 | Burton |
| 5,352,231 A | 10/1994 | Brumfield |
| 5,360,431 A | 11/1994 | Puno |
| 5,385,583 A | 1/1995 | Cotrel |
| 5,397,363 A | 3/1995 | Gelbard |
| 5,429,639 A | 7/1995 | Judet |
| 5,443,467 A | 8/1995 | Biedermann |
| 5,466,237 A | 11/1995 | Byrd, III |
| 5,468,241 A | 11/1995 | Metz Stavenhagen |
| 5,474,555 A | 12/1995 | Puno |
| 5,496,321 A | 3/1996 | Puno |
| 5,520,689 A | 5/1996 | Schlapfer |
| 5,536,268 A | 7/1996 | Griss |
| 5,545,165 A | 8/1996 | Biedermann |
| 5,554,157 A | 9/1996 | Errico |
| 5,569,248 A | 10/1996 | Mathews |
| 5,584,887 A | 12/1996 | Kambin |
| 5,585,020 A | 12/1996 | Becker |
| 5,586,984 A | 12/1996 | Errico |
| 5,589,901 A | 12/1996 | Means |
| 5,605,457 A | 2/1997 | Bailey |
| 5,647,873 A | 7/1997 | Errico |
| 5,649,963 A | 7/1997 | McDevitt |
| 5,651,789 A | 7/1997 | Cotrel |
| 5,667,508 A | 9/1997 | Errico |
| 5,669,911 A | 9/1997 | Errico |
| 5,672,176 A | 9/1997 | Biedermann |
| 5,680,963 A | 10/1997 | Brusko |
| 5,683,390 A | 11/1997 | Metz-Stavenhagen |
| 5,683,391 A | 11/1997 | Boyd |
| 5,690,630 A | 11/1997 | Errico |
| 5,716,356 A | 2/1998 | Biedermann |
| 5,720,751 A | 2/1998 | Jackson |
| 5,725,527 A | 3/1998 | Biedermann |
| 5,733,286 A | 3/1998 | Errico |
| 5,738,685 A | 4/1998 | Halm |
| 5,772,661 A | 6/1998 | Michelson |
| 5,782,833 A | 7/1998 | Haider |
| 5,788,097 A | 8/1998 | McInnes |
| 5,797,911 A | 8/1998 | Sherman |
| 5,810,818 A | 9/1998 | Errico |
| 5,817,094 A | 10/1998 | Errico |
| 5,863,293 A | 1/1999 | Richelsoph |
| 5,873,878 A | 2/1999 | Harms |
| 5,879,350 A | 3/1999 | Sherman |
| 5,882,350 A | 3/1999 | Ralph |
| 5,885,286 A | 3/1999 | Sherman et al. |
| 5,888,221 A | 3/1999 | Gelbard |
| 5,891,145 A | 4/1999 | Morrison et al. |
| 5,899,904 A | 5/1999 | Errico et al. |
| 5,899,905 A | 5/1999 | Errico et al. |
| 5,910,141 A | 6/1999 | Morrison |
| 5,925,047 A | 7/1999 | Errico et al. |
| 5,947,969 A | 9/1999 | Errico et al. |
| 5,961,266 A | 10/1999 | Tseng |
| 5,964,760 A | 10/1999 | Richelsoph |
| 5,976,146 A | 11/1999 | Ogawa et al. |
| 5,984,922 A | 11/1999 | McKay |
| 5,984,923 A | 11/1999 | Breard |
| 5,989,254 A | 11/1999 | Katz |
| 5,989,255 A | 11/1999 | Pepper |
| 6,004,349 A | 12/1999 | Jackson |
| 6,010,503 A | 1/2000 | Richelsoph |
| 6,030,388 A | 2/2000 | Yoshimi |
| 6,033,406 A | 3/2000 | Mathews |
| 6,053,917 A | 4/2000 | Sherman |
| 6,056,753 A | 5/2000 | Jackson |
| 6,059,786 A | 5/2000 | Jackson |
| 6,074,391 A | 6/2000 | Metz-Stavenhagen |
| 6,077,262 A | 6/2000 | Schlapfer |
| 6,083,225 A | 7/2000 | Winslow |
| 6,083,227 A | 7/2000 | Saurat |
| 6,090,110 A | 7/2000 | Metz-Stavenhagen |
| 6,090,111 A | 7/2000 | Nichols |
| 6,099,528 A | 8/2000 | Saurat |
| 6,102,912 A | 8/2000 | Cazin |
| 6,102,913 A | 8/2000 | Jackson |
| 6,113,602 A | 9/2000 | Sand |
| 6,120,760 A | 9/2000 | Hotten |
| 6,132,431 A | 10/2000 | Nilsson |
| 6,132,432 A | 10/2000 | Richelsoph |
| 6,139,549 A | 10/2000 | Keller |
| 6,139,551 A | 10/2000 | Michelson |
| 6,183,472 B1 | 2/2001 | Lutz |
| 6,224,598 B1 | 5/2001 | Jackson |
| 6,226,548 B1 | 5/2001 | Foley |
| 6,235,028 B1 | 5/2001 | Brumfield |
| 6,251,112 B1 | 6/2001 | Jackson |
| 6,254,602 B1 | 7/2001 | Justis |
| 6,258,090 B1 | 7/2001 | Jackson |
| 6,261,287 B1 | 7/2001 | Metz-Stavenhagen |
| 6,280,442 B1 | 8/2001 | Barker |
| 6,296,642 B1 | 10/2001 | Morrison |
| 6,299,616 B1 | 10/2001 | Beger |
| 6,302,633 B1 | 10/2001 | Poe |
| 6,315,564 B1 | 11/2001 | Levisman |
| 6,331,179 B1 | 12/2001 | Freid |
| 6,355,040 B1 | 3/2002 | Richelsoph |
| 6,358,254 B1 | 3/2002 | Anderson |
| 6,361,535 B2 | 3/2002 | Jackson |
| 6,368,321 B1 | 4/2002 | Jackson |
| 6,371,989 B1 | 4/2002 | Chauvin |
| 6,379,356 B1 | 4/2002 | Jackson |
| 6,387,097 B1 | 5/2002 | Alby |
| 6,416,515 B1 | 7/2002 | Wagner |
| 6,428,541 B1 | 8/2002 | Boyd |
| 6,440,132 B1 | 8/2002 | Jackson |
| 6,440,133 B1 | 8/2002 | Beale |
| 6,440,137 B1 | 8/2002 | Horvath |
| 6,443,953 B1 | 9/2002 | Perra |
| 6,454,768 B1 | 9/2002 | Jackson |
| 6,454,772 B1 | 9/2002 | Jackson |
| 6,458,131 B1 | 10/2002 | Ray |
| 6,458,132 B2 | 10/2002 | Choi |
| 6,468,276 B1 | 10/2002 | McKay |
| 6,471,705 B1 | 10/2002 | Biedermann |
| 6,475,218 B2 | 11/2002 | Gournay |
| 6,478,795 B1 | 11/2002 | Gournay |
| 6,485,220 B2 | 11/2002 | Hecht |
| 6,485,491 B1 | 11/2002 | Farris |

| | | |
|---|---|---|
| 6,485,518 B1 | 11/2002 | Cornwall |
| 6,487,798 B2 | 12/2002 | Sueshige |
| 6,488,681 B2 | 12/2002 | Martin |
| 6,488,682 B2 | 12/2002 | Kikuchi |
| 6,488,683 B2 | 12/2002 | Lieberman |
| 6,520,990 B1 | 2/2003 | Ray |
| 6,524,315 B1 | 2/2003 | Selvitelli |
| 6,530,028 B1 | 3/2003 | Yokoyama |
| 6,530,929 B1 | 3/2003 | Justis |
| 6,537,276 B2 | 3/2003 | Metz-Stavenhagen |
| 6,540,748 B2 | 4/2003 | Lombardo |
| 6,540,749 B2 | 4/2003 | Schäfer |
| 6,554,831 B1 | 4/2003 | Rivard |
| 6,554,834 B1 | 4/2003 | Crozet |
| 6,641,586 B2 | 11/2003 | Varieur |
| 6,648,888 B1 | 11/2003 | Shluzas |
| 6,652,527 B2 | 11/2003 | Zucherman |
| 6,660,006 B2 | 12/2003 | Markworth |
| 6,723,100 B2 | 4/2004 | Biedermann |
| 6,726,689 B2 | 4/2004 | Jackson |
| 6,730,089 B2 | 5/2004 | Jackson |
| 6,740,086 B2 | 5/2004 | Richelsoph |
| 6,740,089 B2 | 5/2004 | Haider |
| 6,743,231 B1 | 6/2004 | Gray |
| 6,755,829 B1 | 6/2004 | Bono |
| 6,793,656 B1 | 9/2004 | Mathews |
| 6,802,844 B2 | 10/2004 | Ferree |
| 6,821,277 B2 | 11/2004 | Teitelbaum |
| 6,837,889 B2 | 1/2005 | Shluzas |
| 6,905,500 B2 | 6/2005 | Jeon |
| 6,911,030 B1 | 6/2005 | Vanacker |
| 6,951,538 B2 | 10/2005 | Ritland |
| 7,008,422 B2 | 3/2006 | Foley |
| 7,008,424 B2 | 3/2006 | Teitelbaum |
| 7,011,660 B2 | 3/2006 | Sherman |
| 7,081,117 B2 | 7/2006 | Bono |
| 7,125,426 B2 | 10/2006 | Moumene |
| 7,156,850 B2 | 1/2007 | Kim |
| 7,160,300 B2 | 1/2007 | Jackson |
| 7,179,261 B2 | 2/2007 | Sicvol |
| 7,186,255 B2 | 3/2007 | Baynham |
| 7,188,626 B2 | 3/2007 | Foley |
| 7,250,052 B2 | 7/2007 | Landry |
| 7,261,714 B2 | 8/2007 | Richelsoph |
| 7,491,218 B2 | 2/2009 | Landry |
| 7,527,638 B2 | 5/2009 | Anderson |
| 7,666,188 B2 | 2/2010 | Anderson |
| 2001/0001119 A1 | 5/2001 | Lombardo |
| 2001/0010000 A1 | 7/2001 | Gertzbein |
| 2001/0023350 A1 | 9/2001 | Choi |
| 2001/0025180 A1 | 9/2001 | Jackson |
| 2001/0034521 A1 | 10/2001 | Bailey |
| 2002/0007183 A1 | 1/2002 | Lee |
| 2002/0010467 A1 | 1/2002 | Cooper |
| 2002/0013585 A1 | 1/2002 | Gournay |
| 2002/0022842 A1 | 2/2002 | Horvath |
| 2002/0026192 A1 | 2/2002 | Schmiel |
| 2002/0026193 A1 | 2/2002 | Barker |
| 2002/0032443 A1 | 3/2002 | Sherman |
| 2002/0035366 A1 | 3/2002 | Walder |
| 2002/0040243 A1 | 4/2002 | Attali |
| 2002/0045898 A1 | 4/2002 | Freid |
| 2002/0049444 A1 | 4/2002 | Knox |
| 2002/0055739 A1 | 5/2002 | Lieberman |
| 2002/0058942 A1 | 5/2002 | Biedermann |
| 2002/0068938 A1 | 6/2002 | Jackson |
| 2002/0068940 A1 | 6/2002 | Gaines |
| 2002/0082602 A1 | 6/2002 | Biedermann |
| 2002/0087188 A1 | 7/2002 | Pedlick |
| 2002/0091386 A1 | 7/2002 | Martin |
| 2002/0095153 A1 | 7/2002 | Jones |
| 2002/0111626 A1 | 8/2002 | Ralph |
| 2002/0111628 A1 | 8/2002 | Ralph |
| 2002/0116000 A1 | 8/2002 | Zucherman |
| 2002/0116001 A1 | 8/2002 | Schafer |
| 2002/0120272 A1 | 8/2002 | Yuan |
| 2002/0133154 A1 | 9/2002 | Saint Martin |
| 2002/0138076 A1 | 9/2002 | Biedermann |
| 2002/0138077 A1 | 9/2002 | Ferree |

| | | | |
|---|---|---|---|
| 2002/0143341 A1 | 10/2002 | Biedermann | |
| 2002/0161368 A1 | 10/2002 | Foley | |
| 2002/0169448 A1 | 11/2002 | Vanacker | |
| 2002/0169450 A1 | 11/2002 | Lange | |
| 2002/0173791 A1 | 11/2002 | Howland | |
| 2002/0183747 A1 | 12/2002 | Jao | |
| 2002/0183748 A1 | 12/2002 | Martin | |
| 2002/0183749 A1 | 12/2002 | Burgess | |
| 2002/0188295 A1 | 12/2002 | Martz | |
| 2003/0004511 A1 | 1/2003 | Ferree | |
| 2003/0004512 A1 | 1/2003 | Farris | |
| 2003/0009168 A1 | 1/2003 | Beale | |
| 2003/0023240 A1 | 1/2003 | Amrein | |
| 2003/0023243 A1 | 1/2003 | Biedermann | |
| 2003/0028190 A1 | 2/2003 | Patel | |
| 2003/0032957 A1 | 2/2003 | McKinley | |
| 2003/0045875 A1 | 3/2003 | Bertranou | |
| 2003/0045879 A1 | 3/2003 | Minfelde | |
| 2003/0050640 A1 | 3/2003 | Lee | |
| 2003/0055426 A1 | 3/2003 | Carbone | |
| 2003/0055427 A1 | 3/2003 | Graf | |
| 2003/0060823 A1 | 3/2003 | Bryan | |
| 2003/0060824 A1 | 3/2003 | Viart | |
| 2003/0060826 A1 | 3/2003 | Foley | |
| 2003/0069603 A1* | 4/2003 | Little et al. .................... | 606/219 |
| 2003/0083657 A1 | 5/2003 | Drewry | |
| 2003/0100896 A1 | 5/2003 | Biedermann | |
| 2003/0100904 A1 | 5/2003 | Biedermann | |
| 2003/0130659 A1 | 7/2003 | Haider | |
| 2003/0199873 A1 | 10/2003 | Richelsoph | |
| 2003/0199884 A1 | 10/2003 | Davison | |
| 2003/0208203 A1 | 11/2003 | Lim | |
| 2003/0216748 A1 | 11/2003 | Gitis | |
| 2003/0216768 A1 | 11/2003 | Gitis | |
| 2003/0225408 A1 | 12/2003 | Nichols | |
| 2003/0229347 A1 | 12/2003 | Sherman | |
| 2004/0014326 A1 | 1/2004 | Din | |
| 2004/0039384 A1 | 2/2004 | Boehm | |
| 2004/0049191 A1 | 3/2004 | Markworth | |
| 2004/0092932 A1* | 5/2004 | Aubin et al. .................... | 606/61 |
| 2004/0138662 A1 | 7/2004 | Landry | |
| 2004/0143265 A1 | 7/2004 | Landry | |
| 2004/0162560 A1 | 8/2004 | Raynor | |
| 2004/0172022 A1 | 9/2004 | Landry | |
| 2004/0181224 A1 | 9/2004 | Biedermann | |
| 2004/0193160 A1 | 9/2004 | Richelsoph | |
| 2004/0204711 A1 | 10/2004 | Jackson | |
| 2004/0215190 A1 | 10/2004 | Nguyen | |
| 2004/0243139 A1 | 12/2004 | Lewis | |
| 2004/0267275 A1 | 12/2004 | Cournoyer | |
| 2005/0001022 A1 | 1/2005 | Fieser | |
| 2005/0010219 A1 | 1/2005 | Dalton | |
| 2005/0010221 A1 | 1/2005 | Dalton | |
| 2005/0011383 A1 | 1/2005 | Hadden | |
| 2005/0021031 A1 | 1/2005 | Foley | |
| 2005/0033299 A1 | 2/2005 | Shluzas | |
| 2005/0038432 A1 | 2/2005 | Shaolian | |
| 2005/0038434 A1 | 2/2005 | Mathews | |
| 2005/0065517 A1 | 3/2005 | Chin | |
| 2005/0080418 A1 | 4/2005 | Simonson | |
| 2005/0085813 A1 | 4/2005 | Spitler | |
| 2005/0131408 A1* | 6/2005 | Sicvol et al. .................... | 606/61 |
| 2005/0131421 A1 | 6/2005 | Anderson | |
| 2005/0131422 A1 | 6/2005 | Anderson | |
| 2005/0137594 A1 | 6/2005 | Doubler | |
| 2005/0154389 A1 | 7/2005 | Selover | |
| 2005/0171540 A1 | 8/2005 | Lim | |
| 2005/0171549 A1 | 8/2005 | Boehm | |
| 2005/0182407 A1 | 8/2005 | Dalton | |
| 2005/0182410 A1 | 8/2005 | Jackson | |
| 2005/0192570 A1* | 9/2005 | Jackson .................... | 606/61 |
| 2005/0192571 A1 | 9/2005 | Abdelgany | |
| 2005/0192579 A1 | 9/2005 | Jackson | |
| 2005/0192589 A1 | 9/2005 | Raymond | |
| 2005/0215999 A1 | 9/2005 | Birkmeyer | |
| 2005/0228380 A1 | 10/2005 | Moore | |
| 2005/0234449 A1 | 10/2005 | Aferzon | |
| 2005/0261687 A1 | 11/2005 | Garamszegi | |
| 2005/0273101 A1 | 12/2005 | Schumacher | |

| | | |
|---|---|---|
| 2005/0277934 A1 | 12/2005 | Vardiman |
| 2005/0283245 A1 | 12/2005 | Gordon |
| 2006/0009777 A1 | 1/2006 | Lim |
| 2006/0025771 A1 | 2/2006 | Jackson |
| 2006/0036244 A1 | 2/2006 | Spitler |
| 2006/0036252 A1 | 2/2006 | Baynham |
| 2006/0036255 A1 | 2/2006 | Pond |
| 2006/0058794 A1 | 3/2006 | Jackson |
| 2006/0069391 A1 | 3/2006 | Jackson |
| 2006/0084980 A1 | 4/2006 | Melkent |
| 2006/0084993 A1 | 4/2006 | Landry |
| 2006/0089643 A1 | 4/2006 | Mujwid |
| 2006/0111712 A1 | 5/2006 | Jackson |
| 2006/0111713 A1 | 5/2006 | Jackson |
| 2006/0111714 A1 | 5/2006 | Foley |
| 2006/0111715 A1* | 5/2006 | Jackson ............................ 606/61 |
| 2006/0142761 A1 | 6/2006 | Landry |
| 2006/0149238 A1 | 7/2006 | Sherman |
| 2006/0184178 A1 | 8/2006 | Jackson |
| 2006/0200132 A1* | 9/2006 | Chao et al. ........................ 606/61 |
| 2006/0200135 A1* | 9/2006 | Sherman et al. .................. 606/61 |
| 2006/0229614 A1 | 10/2006 | Foley |
| 2006/0247630 A1 | 11/2006 | Iott |
| 2006/0264942 A1 | 11/2006 | Lim |
| 2006/0293664 A1 | 12/2006 | Schumacher |
| 2006/0293680 A1 | 12/2006 | Jackson |
| 2007/0018549 A1 | 1/2007 | Chai |
| 2007/0049931 A1 | 3/2007 | Justis |
| 2007/0106123 A1 | 5/2007 | Gorek |
| 2007/0129731 A1 | 6/2007 | Sicvol |
| 2007/0179502 A1 | 8/2007 | Raynor |
| 2007/0185491 A1 | 8/2007 | Foley |
| 2007/0191840 A1 | 8/2007 | Pond |
| 2007/0198015 A1 | 8/2007 | Foley |
| 2007/0233079 A1 | 10/2007 | Fallin |
| 2007/0288002 A1 | 12/2007 | Carls |
| 2007/0288026 A1 | 12/2007 | Shluzas |
| 2007/0299443 A1 | 12/2007 | DiPoto |
| 2008/0015584 A1 | 1/2008 | Richelsoph |
| 2008/0082103 A1 | 4/2008 | Hutton |
| 2008/0114403 A1 | 5/2008 | Kuester |
| 2008/0119849 A1 | 5/2008 | Beardsley |
| 2008/0119850 A1 | 5/2008 | Sicvol |
| 2008/0125817 A1 | 5/2008 | Arnett |
| 2008/0262318 A1 | 10/2008 | Gorek |
| 2008/0300638 A1 | 12/2008 | Beardsley |

FOREIGN PATENT DOCUMENTS

| | | |
|---|---|---|
| DE | 3434807 | 7/1987 |
| DE | 3711013 | 6/1988 |
| DE | 198915443 | 7/1990 |
| DE | 199006568 | 12/1990 |
| DE | 3916198 | 7/1992 |
| DE | 4307576 | 4/1994 |
| DE | 199403231 | 6/1994 |
| DE | 3639810 | 4/1998 |
| DE | 29810798 | 12/1999 |
| DE | 10136129 | 2/2003 |
| DE | 10157969 | 2/2003 |
| DE | 10027988 | 8/2003 |
| DE | 19912364 | 10/2004 |
| DE | 202005007495 | 9/2005 |
| EP | 283373 | 9/1988 |
| EP | 346521 | 12/1989 |
| EP | 348272 | 8/1991 |
| EP | 330881 | 10/1991 |
| EP | 242708 | 11/1992 |
| EP | 324022 | 9/1993 |
| EP | 441729 | 1/1994 |
| EP | 379551 | 2/1994 |
| EP | 328883 | 7/1994 |
| EP | 392927 | 8/1995 |
| EP | 572790 | 2/1996 |
| EP | 614649 | 5/1996 |
| EP | 452451 | 6/1996 |
| EP | 528706 | 10/1996 |
| EP | 465158 | 1/1997 |
| EP | 836835 | 7/1998 |
| EP | 870474 | 10/1998 |
| EP | 771635 | 9/2002 |
| EP | 1332722 | 8/2003 |
| EP | 1133951 | 11/2003 |
| EP | 1090595 | 12/2003 |
| EP | 1449486 | 8/2004 |
| EP | 1190678 | 6/2008 |
| EP | 1354563 | 9/2009 |
| FR | 2624720 | 6/1989 |
| FR | 2659546 | 9/1991 |
| WO | WO 8900028 | 1/1989 |
| WO | WO 9000377 | 1/1990 |
| WO | WO 9106254 | 5/1991 |
| WO | WO 9116020 | 10/1991 |
| WO | WO 9220294 | 11/1992 |
| WO | WO 9311715 | 6/1993 |
| WO | WO 9414384 | 8/1994 |
| WO | WO 9501132 | 1/1995 |
| WO | WO 9513755 | 5/1995 |
| WO | WO 9513756 | 5/1995 |
| WO | WO 9514437 | 6/1995 |
| WO | WO 9812977 | 4/1998 |
| WO | WO 0101873 | 1/2001 |
| WO | WO 0269854 | 9/2002 |
| WO | WO 2004041100 | 5/2004 |
| WO | WO 2005006948 | 4/2005 |
| WO | WO 2005041799 | 5/2005 |
| WO | WO 2006042189 | 4/2006 |

OTHER PUBLICATIONS

Moss Miami Spinal System, Brochure "Polyaxial Screw" Dec. 2000.
Synthes Spine, Brochure "USS Fracture System Technique Guide" Sep. 2004.
Zimmer Spine, Silhouelte Spinal Fixation System, Catalog, Mar. 2005, 6 pgs.
"CD Horizon Legacy 5.5 Spinal System" Brochure, Medtronic Sofamor Danek, USA Inc., 2003.
Ebara et al; A New System For the Anterio Restoration and Fixation of Thoracic Spinal Deformities Using an Andoscopic Approach; Spine 200 Apr. 1;pp. 876-83; vol. 25(7).
Glazer et al.; Biomechanical analysis of Multilevel Fixation Methods in the Lumbar Spine; Spine Jan. 15, 1997; pp. 171-82;vol. 22(2).
Jeanneret, Posterior Rod System of the Cervical Spine: A New Implant Allowing Optimal Screw Insertion, Eur. Spine J 1996; pp. 350-6, 5(5):Springer-Verlag.
John R. Walker, "Machining Fundamentals Fundamental Basic to Industry", The Goodheart-Wilcox Co., Inc., 1981, pp. 2,179-186, including redacted version.
Kaneda et al; New Anterior Instrumentation for the Management of Thoracolumbar and Lumbar Scoliosis; Spine May 15, 1996; pp. 1250-61; vol. 21(10).
Lacoe et al., "Machineshop—Operations and Setups", American Technical Society, 1973, pp. 380, 386 and 388 including redacted version.
Ltr to Robert Malone from Dept of Health & Human Services, Jun. 20, 2002 regarding Forex Corporation OPTIMA™ Devices 510(k) Summary, 5 pages.
OPTIMA™ Spinal system Surgical Technique Brochure, pp. 1-17, 2005.
Shapiro et al.; Spinal Instrumentation With a Low Complication Rate; Surg. Neurol. Dec. 1997; pp. 566-74; vol. 48(6) Elsevier Science.
U&I Corporation Thoracolumbar Spine Optima Spinal System from website www.uandi.co.kr pp. 1-2 Nov. 10, 2005.
Viau et al.; Thoracic Pedicle Screw Instrumentation Using the "Funnell Technique"; J. Spinal Discord Tech. Dec. 2002; pp. 450-3; vol. 15(6).
XIA™ Spinal System Brochure, Stryker®, Howmedica Osteonics, pp. 1-7, Stryker Corporation, Rutherford, NJ, 1999.

* cited by examiner

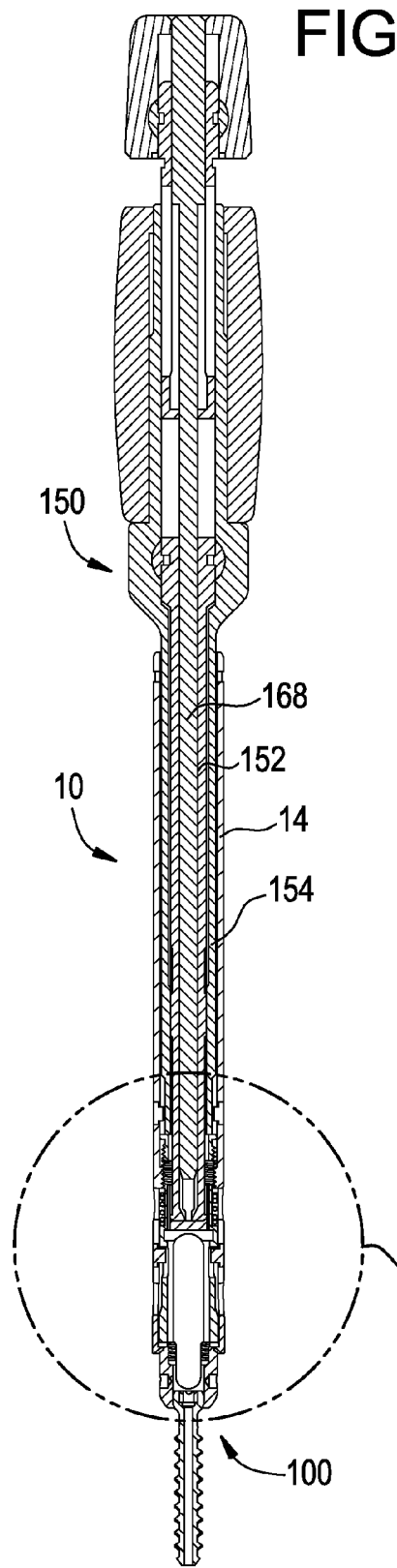
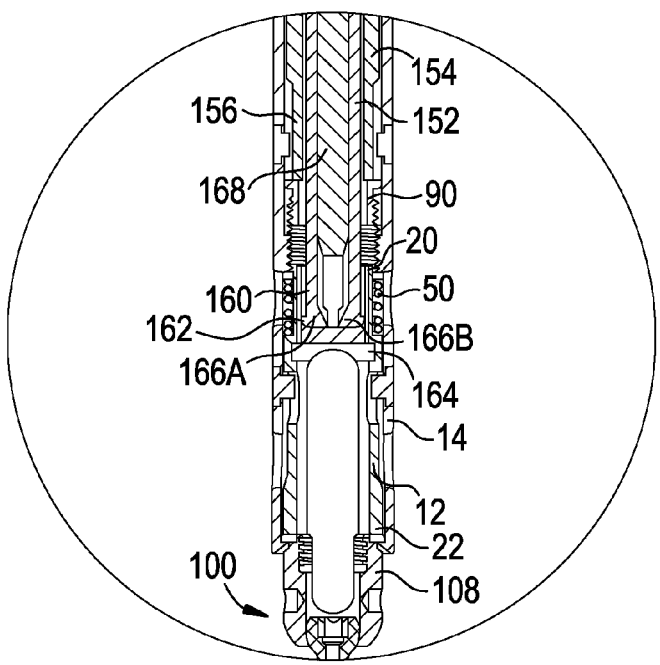

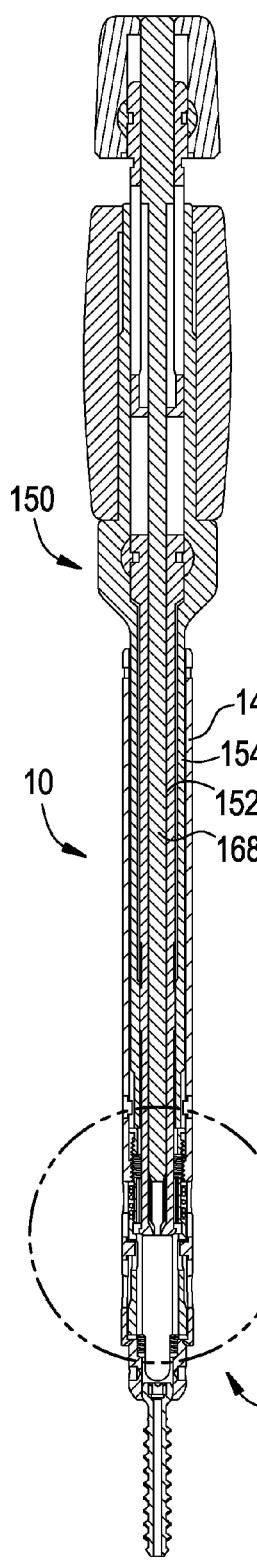
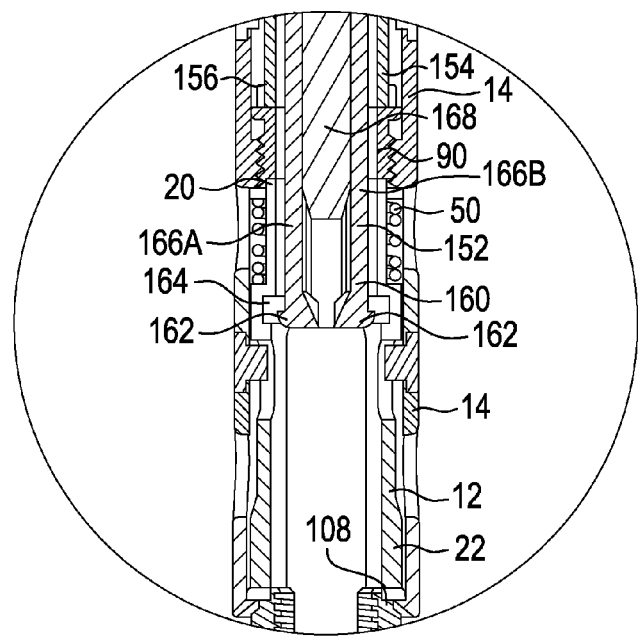
FIG. 6A
FIG. 6B

FIG. 6C
FIG. 6D
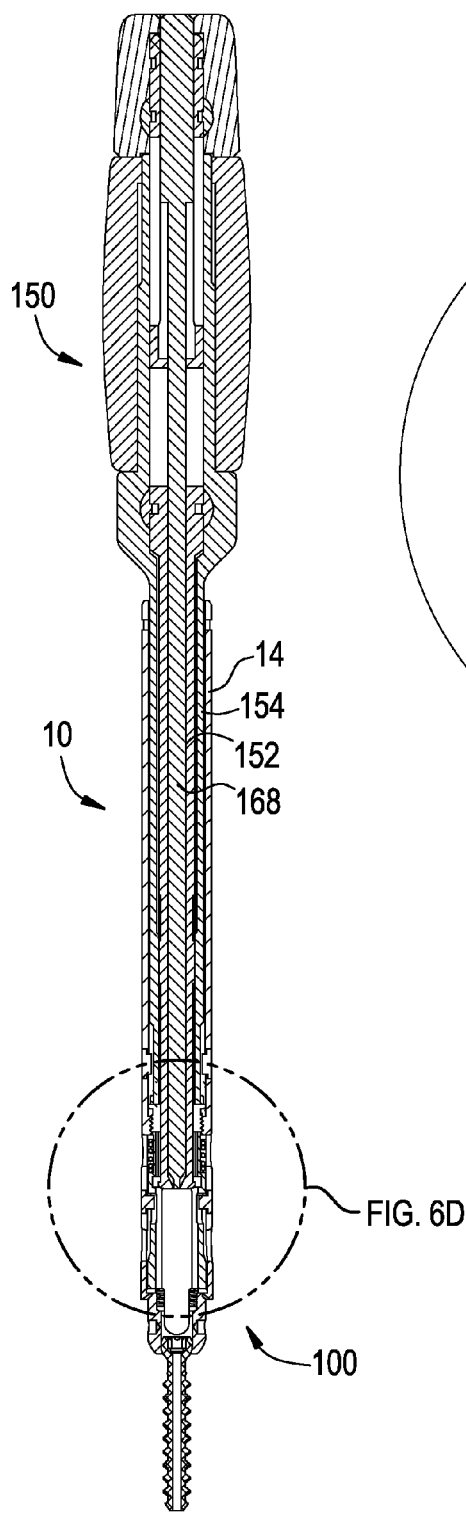
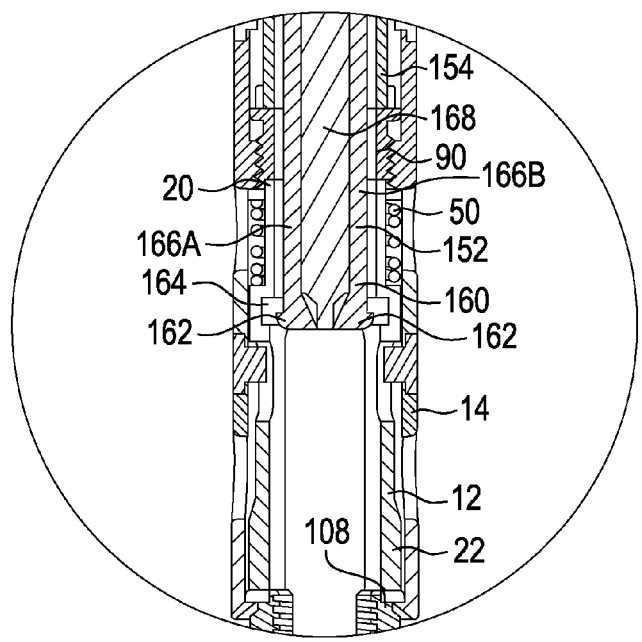

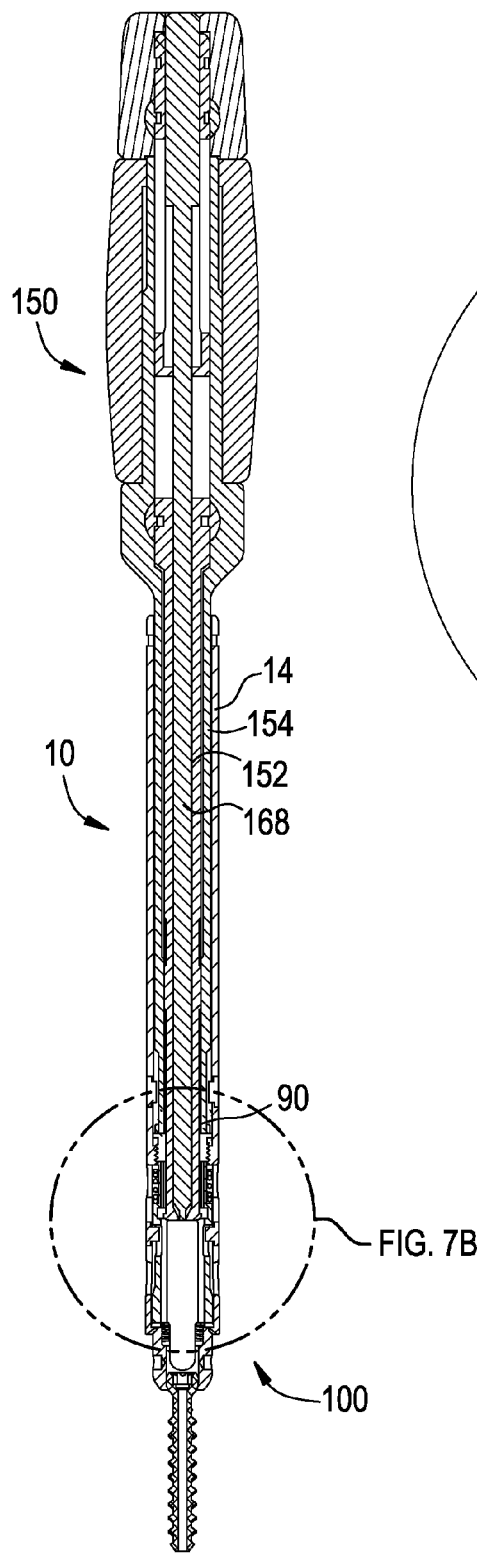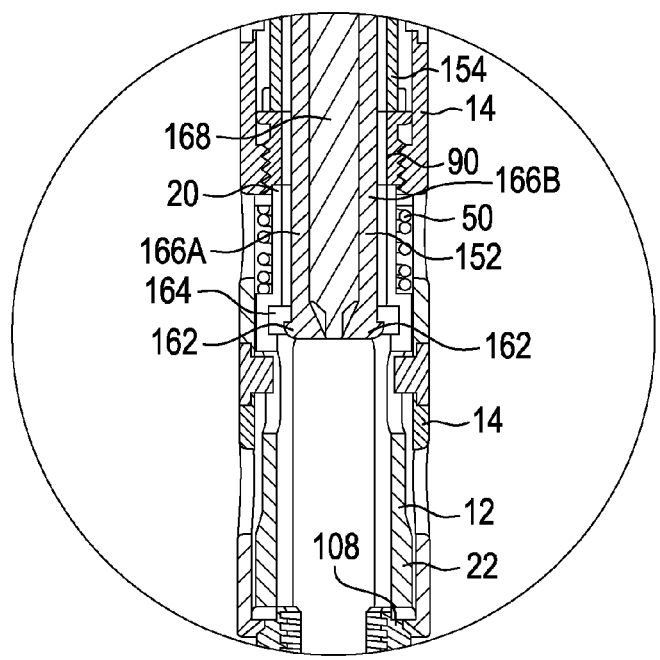

METHODS AND DEVICES FOR MINIMALLY INVASIVE SPINAL CONNECTION ELEMENT DELIVERY

CROSS-REFERENCE TO RELATED APPLICATIONS

This application claims priority to U.S. Provisional Patent Application No. 60/977,490 filed Oct. 4, 2007, which is incorporated herein by reference.

BACKGROUND

Spinal connection elements, such as rods and plates, may be used in spinal surgery to align and fix a desired relationship between two or more vertebrae typically until fusion of the instrumented vertebrae occurs. A spinal connection element may be rigid, inhibiting relative motion of the vertebrae, or dynamic, allowing some degree of relative motion between the vertebrae. A spinal connection element may be coupled to the vertebrae by various bone anchors, including bone screws, hooks, and/or wires.

Recently, the trend in spinal surgery has been to provide less invasive instruments and surgical procedures for delivery of spinal connection elements to bone anchors anchored to the vertebrae to be treated. Less invasive surgical procedures, often referred to as minimally invasive surgical procedures, may decrease damage to surrounding tissue and thereby increase patient recovery time and reduce surgical complications. Present instruments for minimally invasive spine surgery can be difficult to use and difficult to clean. Accordingly, there is need for improved instruments and procedures for minimally invasive spine surgery, in particular for the delivery of spinal connection elements.

SUMMARY

Disclosed herein are methods and devices for the minimally invasive delivery of spinal connection elements, such as dynamic or rigid spinal rods, to one or more bone anchors anchored to a vertebra. An exemplary device for delivery of a spinal rod to a bone anchor may comprise an inner tube and an outer tube disposed about at least a portion of the inner tube. The inner tube may be adjustable relative to the outer tube along the longitudinal axis of the outer tube between a first position and a second position in which the distal end of the inner tube contacts the bone anchor. A spring may be positioned within the outer tube and interposed between the inner tube and the outer tube to bias the inner tube distally. A locking member may be coupled to the outer tube and may be adjustable relative to the outer tube along the longitudinal axis of the outer tube between a proximal position in which the locking member is spaced apart from the inner tube to permit proximal axial movement of the inner tube relative to the outer tube and a distal position in which the locking member inhibits proximal axial motion of the inner tube relative to the outer tube.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the devices and methods disclosed herein and, although not to scale, show relative dimensions.

FIGS. 5A and 5B are side views in cross section of the device of FIG. 1 connected to a bone anchor, illustrating engagement of the instrument of FIG. 4 with the locking member of the device;

FIGS. 6A-6D are side views in cross section of the device of FIG. 1 connected to a bone anchor, illustrating engagement of the instrument of FIG. 4 with the annular groove of the inner tube of the device;

FIGS. 7A and 7B are side views in cross section of the device of FIG. 1 connected to a bone anchor, illustrating proximal adjustment of the inner tube of the device with the instrument of FIG. 4;

DETAIL DESCRIPTION OF EXEMPLARY EMBODIMENTS

Figure 1:
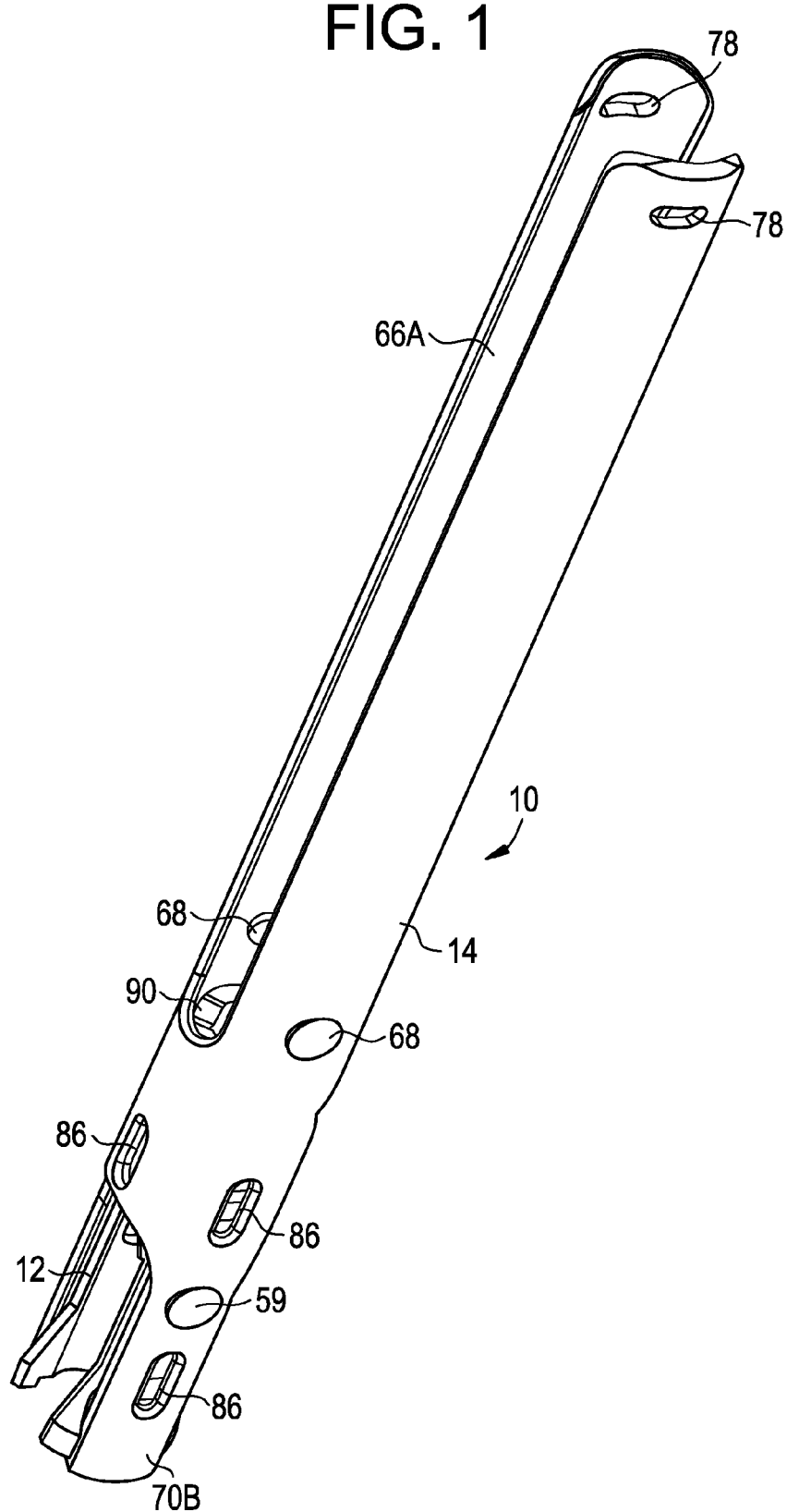
FIG. 1 is a perspective view of a device for delivery of a spinal connection element, such as a spinal rod, to a bone anchor.
Figure 2:
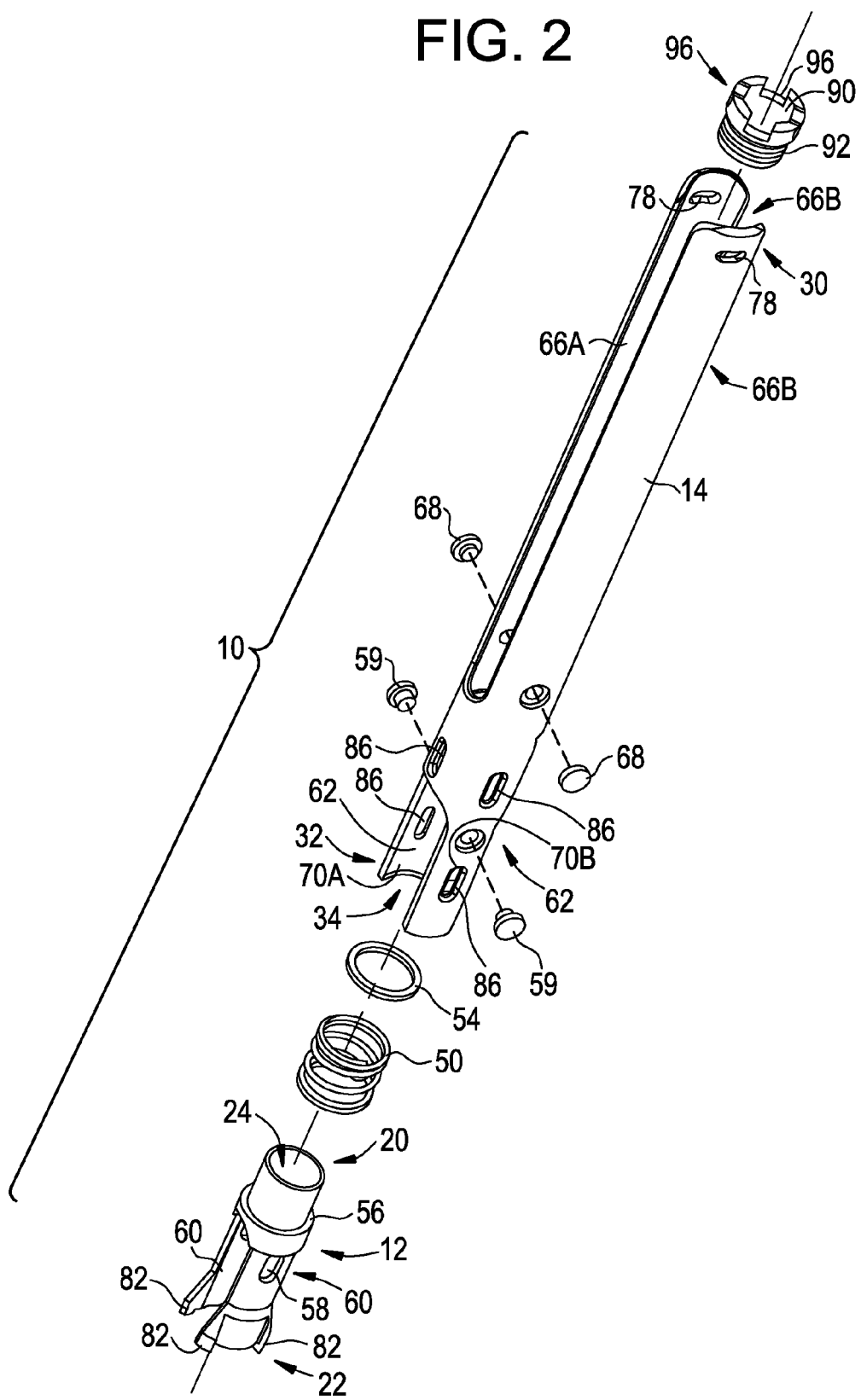
FIG. 2 is an exploded view of the device of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-7 illustrate an exemplary embodiment of a device 10 for delivery of a spinal connection element, such as a rigid or dynamic spinal rod or plate, to a bone anchor. The exemplary device 10 can facilitate the delivery and implanting of a bone anchor, such as the exemplary bone anchor 100 into bone, in particular, one or more vertebrae of the spine. In particular, the exemplary device 10 can facilitate the delivery and implanting of a bone anchor in a minimally invasive manner and can provide a percutaneous pathway between a skin incision in the patient and the bone anchor that may be used to deliver components of the bone anchor, such as the closure mechanism, one or more spinal connection elements, and/or instruments to the bone anchor. The device 10 is preferably adapted to be introduced through a minimally invasive percutaneous incision, which is a relatively small incision that typically has a length less than the diameter or width of the device being inserted therethrough.

The exemplary device 10 includes an inner tube 12 and an outer tube 14 disposed about at least a portion of the inner tube 12. In the illustrated exemplary embodiment, the outer tube 14 is coaxially disposed about the inner tube 12 such that the inner tube 12 and the outer tube 14 share a common longitudinal axis 26, 36. One skilled in the art will appreciate, however, that the outer tube 14 and inner tube 12 need not be coaxially aligned. The inner tube 12 and the outer tube 14, in the exemplary embodiment, are generally cylindrical in shape, having an approximately circular cross-section. One skilled in the art will appreciate, however, the inner tube 12 and the outer tube 14 may have other cross-sectional shapes, including, for example, elliptical or rectilinear. In the exemplary embodiment, the inner tube 12 and outer tube 14 have analogous cross-sections, however, one skilled in the art will appreciate the inner tube 12 and the outer tube 14 can have different cross-sectional shapes. The axial length of the inner tube 12 and outer tube 12 may vary depending on, for example, the patient anatomy, the procedures employed, and/or, that area of the spine in which the device 10 is employed. The inner tube 12 and the outer tube 14 may be linear, as in the exemplary embodiment, or may curved or angled along one or more sections or the entire length thereof. The inner tube 12 and the outer tube 14 may be constructed from any suitable biocompatible material, including, for example, a metal, such as stainless steel, or a polymer, from any conventional method of manufacturing medical devices.

Although the illustrated exemplary embodiment includes an inner tube and an outer tube, one skilled in the art will appreciate that any number of additional tubes may be employed depending on, for example, the type of bone anchor employed and the manner by which the device is releasably engaged to the bone anchor.

Continuing to refer to FIGS. 1-7, the inner tube 12 includes a proximal end 20, a distal end 22, and a lumen 24 extending between the proximal end 20 and the distal end 22. The lumen 24 extends the length of the inner tube 12 and defines a longitudinal axis 26 of the inner tube 12. The outer tube 14 includes a proximal end 30, a distal end 32, and a lumen 34 extending between the proximal end 30 and the distal end 32. The lumen 34 may extend the length of the outer tube 14 and defines a longitudinal axis 36 of the outer tube 14. The inner tube 12 in positionable within the lumen 34 of the outer tube 14 and, in the exemplary device 10, the inner tube 12 is longitudinally adjustable with respect to the outer tube 14 between a proximal first position in which the distal end 22 of the inner tube 12 is spaced from the bone anchor and a distal second position in which the distal end 22 of the inner tube 12 contacts the bone anchor. The inner tube 12 of the exemplary device 10 is truncated compared to the outer tube 14 of the device 10 and is positioned within the distal end 22 of the outer tube 14.

The inner tube 12 may have one or more sidewall openings or slots 60 formed therein. In the illustrated exemplary embodiment, the inner tube 12 includes two opposed slots 60 that extend longitudinally from the distal end 22 of the inner tube 12. Like the inner tube 12, the outer tube 14 may have one or more sidewall openings or slots 62 formed therein. In the illustrated exemplary embodiment, the outer tube 14 includes two opposed slots 62 that extend longitudinally from the distal end 32 of the inner tube 12. The slots 60 and 62 can be used to facilitate positioning of a spinal connection element, such as a rigid or dynamic spinal rod or a plate, relative to one or more bone anchors. Methods and devices for spinal connection element placement are disclosed in U.S. Patent Application Publication No. 2005/0131421 and U.S. Patent Application Publication No. 2005/0131422, both of which are incorporated herein in by reference. To facilitate positioning of a spinal connection element, the slots 60 and the slots 62 are preferably aligned with one another along at least a portion of the longitudinal axis of the percutaneous access device 10. The width and length of the slot 60 and slot 62 may be varied depending on the particular methods, instruments, and connection elements being employed. In one exemplary embodiment illustrated in FIGS. 8 and 9 and discussed in more detail below, for example, the length of the slots 60 and 62 is selected to span at least from the skin incision to the distal end of the inner tube 12 and the outer tube 14, respectively. In such embodiments, the slots 60 and 62 may be accessible from outside of the patient. In another exemplary embodiment, for example, the device illustrated in FIGS. 1-7B, the length of the slots 60 and 62 is selected to span from the distal end of the inner tube 12 and the outer tube 14, respectively, to a point distal to the skin incision. In such embodiments, the slots 60 and 62 may be accessible only from the lumens of the inner and outer tubes.

In embodiments in which multiple slots are employed, the slots 60, 62 need not be similarly sized (width and/or length). For example, the one or more slots 60 may be sized differently than the one or more slots 62, the one or more of the slots 60 on the inner tube may be sized differently than other slots 60, and/or one or more of the slots 62 on the outer tube may be sized differently than other slots 62. Although the exemplary embodiment includes two opposing slots on the inner tube 12 and the outer tube 14, respectively, one skilled in the art will appreciate that any number of slots may be provided, e.g., no slots, one, two, three, etc. slots, may be provided depending on the method, instruments, and/or connection element employed.

The outer tube 14 of the device 10 may include proximal slots 66A-B that are open at proximal end 30 of the outer tube 14 and extend distally from the proximal end 30 of the outer tube 14. The proximal slots 66A-B facilitate pivoting of the spinal rod in position relative to the bone anchor by accommodating a rod delivery instrument.

The distal end 32 of the outer tube 14 may include a plurality of instrument engagement features to facilitate engagement of an instrument, such as a reduction instruments or a compression/distraction instrument, to the device 10. The instrument engagement features may be a plurality of flat surfaces provided at spaced apart locations on the outer surface of the outer tube 12. The instrument engagement features may be one or more openings 78 provided at spaced apart locations on the outer surface of the outer tube 12. In the exemplary embodiment, the instrument engagement features are a pair of diametrically opposed openings 78.

The inner tube 12 and the outer tube 14 may include a plurality of cleaning openings 86 therein to facilitate cleaning of the device 10.

Referring to FIGS. 1-7, the device 10 is preferably releasably engageable to a bone anchor. In the exemplary embodiment, the outer tube 14 may be releasably engaged to a bone anchor, such as bone anchor 100. For example, the outer tube 14 may be engaged to a bone anchor in a manner that allows the device 10 to be connected to the bone anchor 100 during use, e.g., during implantation and/or delivery and/or fastening of a spinal connection element to the bone anchor, and allows the device to be disconnected from the bone anchor 100 at the conclusion of the procedure. Preferably, the device 10 can be disconnected remotely. For example, in the exemplary embodiment, the device 10 can be disconnected from the bone anchor by accessing the lumen 34 of the outer tube 14 of the device 10 from the proximal end 30 of the outer tube 14, as discussed in more detail below.

The distal end 32 of the outer tube 14 includes a pair of opposed longitudinally extending tabs 70A and 70B that may releaseable engage a bone anchor. In the exemplary embodiment, the tabs 70A and 70B are defined by the sidewalls of the outer tube 14 and are separated by slots 62. In certain exemplary embodiments, the tabs 70A and 70B may be flexible and resilient in the radial direction to facilitate connection to a bone anchor. For example, the tabs 70A and 70B may be flexed apart in the radial direction from a first, relaxed position to facilitate advancement of the tabs longitudinally over a portion of the bone anchor. Once positioned about a portion of the bone anchor, the tabs 70A and 70B may provide a radially compressive force on the bone anchor as the tabs 70A and 70B attempt to return to the first, relaxed position. In other exemplary embodiments the tabs 70A and 70B need not be flexible and resilient. The tabs 70A and 70B each may include a distal angled surface 71A and 71B to facilitate positioning of the tabs 70A and 70B about the bone anchor. In the illustrated embodiment, the distal angled surfaces 71A and 71B extend from a radially outward, distal end to a radially inward, proximal end. In this orientation, the distal angled surfaces 71A and 71B act to separate the tabs 70A and 70B during distal advancement of the outer tube 14 about the bone anchor.

In the illustrated exemplary embodiment, each tab 70A and 70B may include one or more radially inward facing projection 72A, 72B for engagement with a connection feature on a bone anchor. For example, the projection 72A, 72B may be sized and shaped to seat within an opening provided in a portion of the bone anchor. The size, shape and number of projections can be varied depending on, for example, the opening(s) provided on the bone anchor and type of connection desired. In the illustrated exemplary embodiment, for example, each projection 72A, 72B is generally arcuate in shape and has a cross section that is complementary to an arcuate groove 130 provided in the spinal connection element receiving member 108 of the exemplary bone anchor 100. Exemplary configurations for the projections and the corresponding connection features on the bone anchor are described in U.S. Patent Application Publication No. 2005/0131408, which is incorporated herein by reference.

Referring to FIGS. 1-7, the distal end 22 of the inner tube 12 may include a contact surface 81 that contacts at least a portion of a bone anchor when the inner tube 12 is adjusted relative to the outer tube 14 to the second position in which the inner tube 12 contacts the bone anchor. In the illustrated exemplary embodiment, for example, the distal end 22 of the inner tube 12 may have two opposing generally arcuate contact surfaces 81. The contact surfaces 81, in the exemplary embodiment, are oriented approximately perpendicular to the longitudinal axis of the inner tube 12. In the illustrated exemplary embodiment, the contact surfaces 81 are configured to contact a generally arcuate contact surface provided on the proximal end of the receiving member of the exemplary bone anchor 100. Preferably, each contact surface 81 is complementary in size, shape, and orientation to the contact surface on the bone anchor. One skilled in the art will appreciate that the configuration of the contact surface 81, e.g., number, size, shape, and orientation of the contact surface 81, may be varied to, for example, suit the bone anchor being employed.

The distal end 22 of the inner tube 12 and/or the distal end 32 of the outer tube 14 may be configured to inhibit rotation of the bone anchor relative to the device 10. For example, the distal end 22 of the inner tube may include one or more finger-like extensions 82 that extend approximately axially from the distal end 22 of the inner tuber 12 and engage a bone anchor to inhibit rotation of the bone relative to the device. For example, one or more of the extensions 82 may seat within a groove, recess, slot, or similar structure provided in the bone anchor. These extensions 82 also extend radially outward, straddling outer tube 14 and rotationally coupling them.

The device 10 may include a spring 50 positioned within the outer tube 14 and interposed between the inner tube 12 and the outer tube 14 to bias the inner tube 12 distally to, for example, the second position. The spring 50 may be interposed between the inner tube 12 and a shoulder 52 provided on an inner surface of the outer tube 14. A washer 54 may be interposed between the spring 50 and the shoulder 52, as in the exemplary embodiment, or the spring 50 may directly contact the shoulder 50. The spring 50 may be positioned about a portion of the inner tube 12, for example the proximal end 20 of the inner tube 12, and may engage a shoulder 56 on an outer surface of the inner tube 14. In the exemplary embodiment, the spring is positioned about the proximal end 20 of the inner tube 12, a distal end of the spring 50 abuts the shoulder 56 on the inner tube 12, and a proximal end of the spring 50 abuts the washer 54 interposed between the spring 50 and the shoulder 52 on the outer tube 14.

The device 10 may include one or more mechanisms to oppose the spring force from the spring 50 and to retain the inner tube 12 within the outer tube 14. The mechanisms may include, for example, one or more retaining slots 58 oriented along the longitudinal axis of the inner tube 12 each of which receives a projection 59, such as a pin or the like, from an inner surface of the outer tube 14. The length of the retaining slot 58 may be selected to provide the desired extent or limit of longitudinal adjustment of the inner tube 12 relative to the outer tube 14. In the exemplary embodiment a pair of diametrically opposed retaining slots 58 are provided although any number of slots may be provided. The retaining slot 58 and the projection 59 received within the retaining slot may also inhibit relative rotation of the inner tube 12 and outer tube 14. Other mechanisms for retaining the inner tube 12 may include the radial inward projections 72A and 72B. For example, in the exemplary embodiment, the distal end 22 of the inner tube 12 is biased by the spring 50 into abutment with each of the projections 72A and 72B.

Continuing to refer to FIGS. 1-7, the device 10 may include a locking member 90 coupled to the outer tube 14 and adjustable relative to the outer tube 14 along the longitudinal axis of the outer tube 14 between a proximal position in which the locking member 90 is spaced apart from the inner tube 12 to permit proximal axial movement of the inner tube 12 relative to the outer tube 14 and a distal position in which the locking member 90 inhibits proximal axial motion of the inner tube 12 relative to the outer tube 14. The locking member 90 may be positioned within the lumen 34 of the outer tube 14, as in the exemplary embodiment, or may be external to the outer tube 14. In the exemplary embodiment, the locking member 90 includes external threads 92 that engage internal threads 94 provided within the outer tube 14. The locking member 90 may include one or more instrument engagement features 96 to facilitate adjustment of the locking member 90 with an instrument. In the exemplary embodiment, the locking member 90 is a castle nut. On or more retaining pins 68 may be positioned within an opening in the outer tube 14 and may extend into the inner tube 12 to engage the locking member 90 and retain the locking member 90 within the outer tube 14.

Figure 3A:
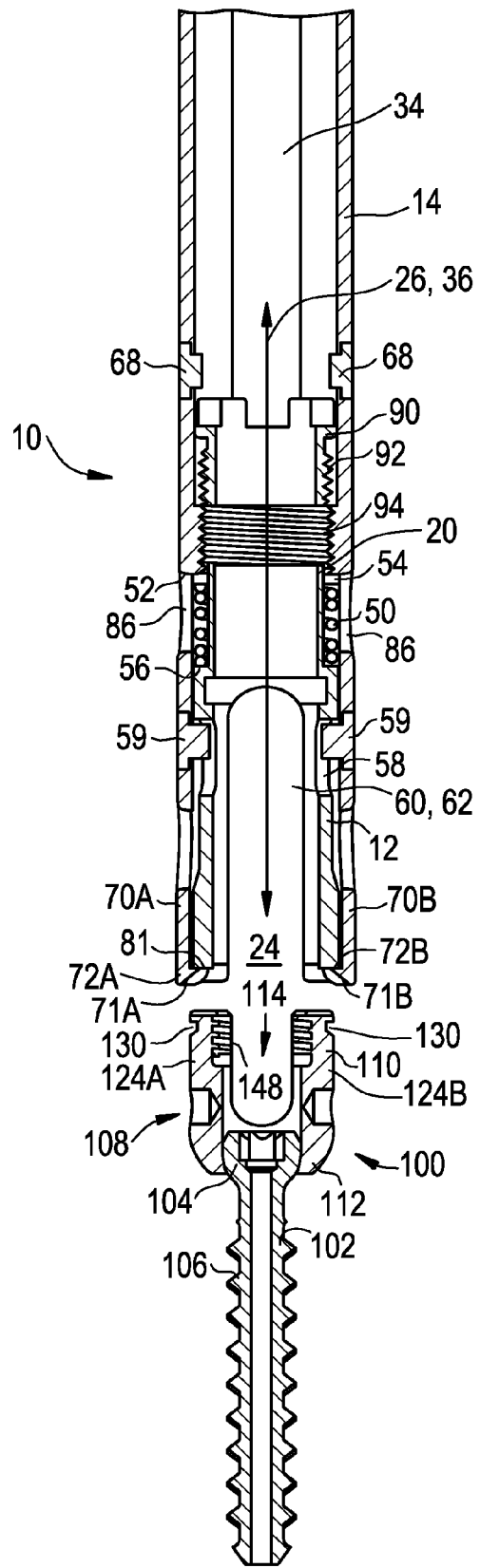
FIGS. 3A-3C are side views in cross section of the device of FIG. 1 illustrating connection of the device to a bone anchor.
Figure 3B:
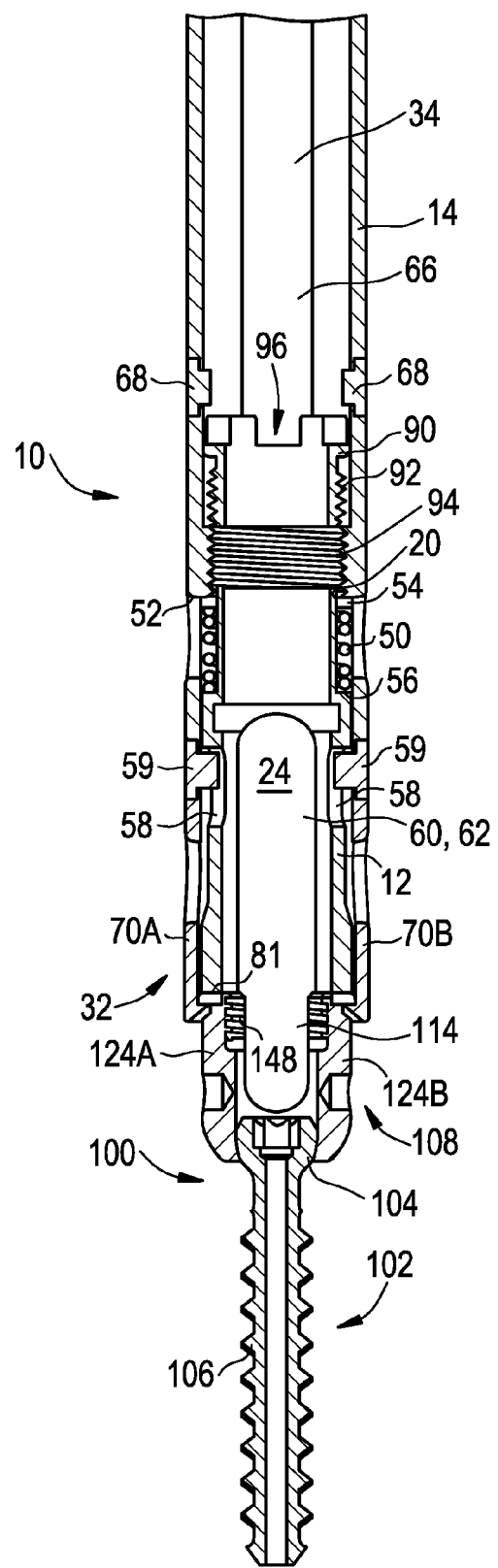
Figure 3C:
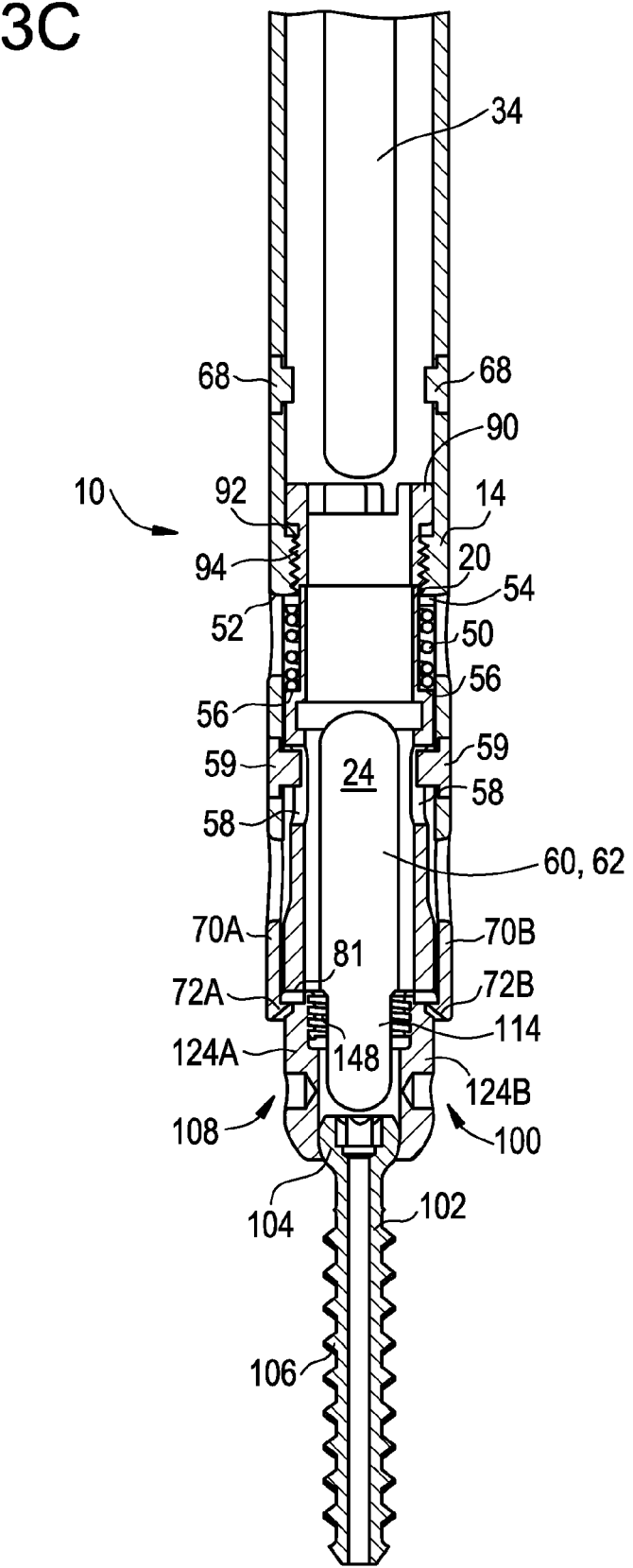
Figure 4:
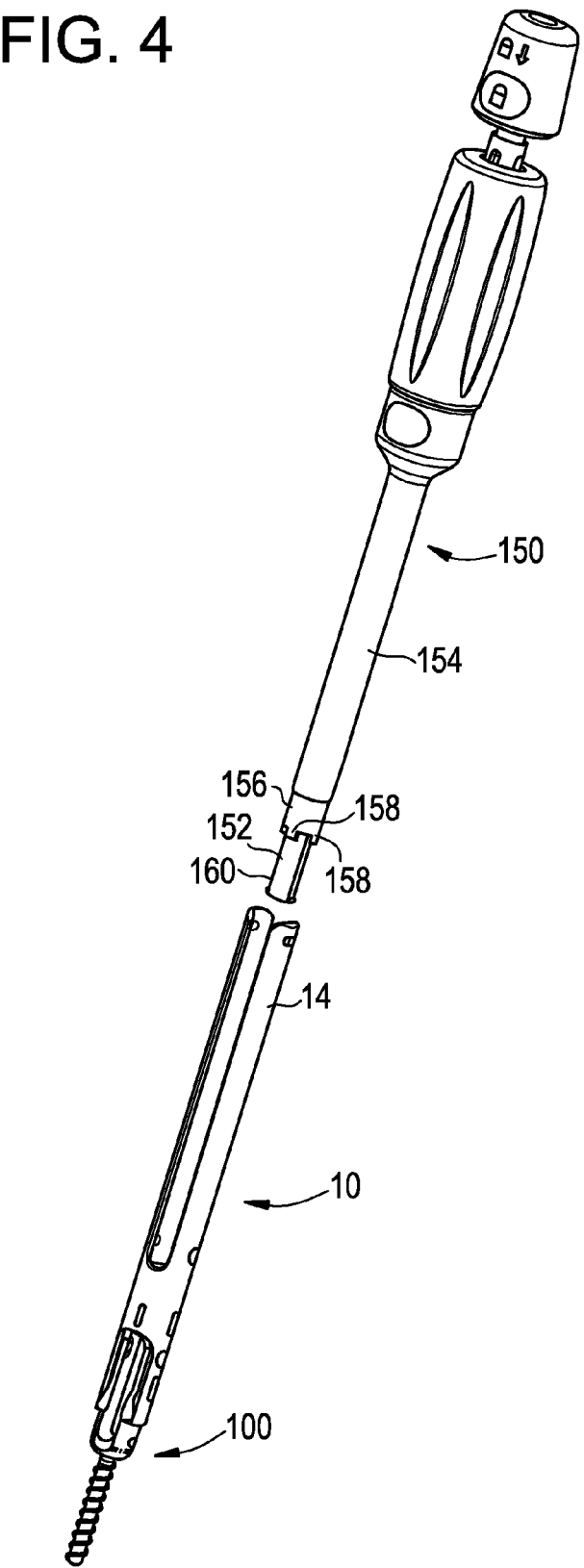
FIG. 4 is a perspective view of the device of FIG. 1 and an instrument for connection and removal of the device to a bone anchor.

FIGS. 3A-3C illustrate an exemplary embodiment of a bone anchor 100 that is particularly suited for use with the exemplary device 10 described herein. One skilled in the art will appreciate, however, that the devices disclosed herein are not limited to use with the exemplary bone anchor 100 but instead may be configured for use with any type of bone anchor, e.g., bone screw or hook; mono-axial, uniplanar or polyaxial. Exemplary bone anchor 100 includes a bone screw 102, such as a pedicle screw, having a proximal head 104 and a distal bone engaging portion 106, which in the illustrated exemplary embodiment is an externally threaded screw shank. The exemplary bone screw assembly 100 also includes a receiving member 108 that is configured to receive and couple a spinal connection element, such as a spinal rod or spinal plate, to the bone anchor 100. The receiving member 108 may be coupled to the bone anchor 102 in any well-known conventional manner. For example, the bone anchor may be poly-axial, as in the present exemplary embodiment in which the bone anchor 102 may be adjustable to multiple angles relative to the receiving member 108, or the bone anchor may be mono-axial, e.g., the bone anchor 102 may fixed relative to the receiving member 108. Exemplary poly-axial bone screws are the EXPEDIUM Polyaxial Pedicle Screws and the VIPER Polyaxial Pedicle Screws, which are available from DePuy Spine, Inc. of Raynham, Mass.

The receiving member 108 of the illustrated exemplary embodiment includes a proximal end 110, a distal end 112, and a recess or slot 114 for receiving a spinal connection element such as a spinal rod. In the exemplary embodiment, the receiving member 108 has a generally U-shaped cross-section defined by two legs 124A and 124B separated by recess 114. Each leg 124A, 124B is free at the proximal end 110 of the receiving member 108. The receiving member 108 may be configured to receive a closure mechanism that locks a spinal connection element within the recess 114. The closure mechanism may be a set screw that is advanceable through the receiving member 108 and may directly or indirectly engage the spinal connection element. For example, the closure mechanism may have external threads that engage internal threads 148 provided in the receiving member 108, e.g., on the legs 124A,B, as in the exemplary embodiment. Any type of conventional closure mechanism may be employed, including, for example, set-screws, non-threaded caps, multi-component closure mechanisms, and/or external nuts.

FIGS. 3A-3B further illustrate an exemplary method of connecting the device 10 to the bone anchor 100. FIG. 3A illustrates the device 10 prior to connection to the bone anchor 100. The locking member 90 is in a proximal position in which the locking member 90 is spaced apart from the proximal end 20 of the inner tube 12 and the inner tube 12 may be adjusted relative to the outer tube 14. The spring 50 biases the inner tube 12 distally into abutment with the proximal surfaces of the projections 72A, 72B of each of the tabs 70A, 70B of the outer tube 14.

FIG. 3B illustrates the outer tube 14 of the device 10 connected to the bone anchor 100. The distal end 32 of the outer tube 14 is advanced over the proximal end of the receiving member 108 of the bone anchor 100. During advancement, the angled surfaces 71A and 71B contact the proximal surface of the receiving member 108 of the bone anchor and cause the tabs 70A and 70B to flex apart thereby facilitating connection of the outer tube 14 to the bone anchor 100. As the outer tube 14 is advanced, the contact surfaces 81 on the distal end 22 of the inner tube 12 engage the proximal end of the receiving member 108 of the bone anchor 100 and the inner tube 12 is moved proximally relative to the outer tube 12 in opposition to the spring force from the spring 50. Advancement of the outer tube 14 may continue until the projections 72A and 72B are seated within the arcuate grooves 130 of the receiving member 108 of the bone anchor 100. Once the outer tube 14 is connected to the receiving member 108 of the bone anchor by the projections 72A and 72B, the spring force from spring 50 maintains the contact surfaces 81 on the distal end 22 of the inner tube 12 in engagement with the proximal end of the receiving member 108 of the bone anchor 100 thereby providing a provisional connection of the device 10 to the bone anchor 100. The locking member 90 is in a proximal position in which the locking member 90 is spaced apart from the inner tube 12 to permit proximal axial movement of the inner tube 12 relative to the outer tube 14. As the inner tube 12 remains adjustable relative to the outer tube 14, the device 10 may be easily removed from the bone anchor 100.

FIG. 3C illustrates the device 10 locked to the bone anchor 100. The locking member 90 is adjusted relative to the inner tube 12 to inhibit proximal movement of the inner tube 12 relative to the outer tube 14 and thereby lock the device 10 firmly to the bone anchor 100. In the exemplary embodiment, the locking member 90 is advanced within the lumen 34 of the outer tube 14 to a distal position in which the locking member 90 abuts the proximal end 20 of the inner tube 12 and inhibits proximal axial motion of the inner tube 12 relative to the outer tube 14.

The device 10 may be connected to the exemplary bone anchor 100, or another bone anchor, before implantation of the bone anchor or after the bone anchor is implanted into the patient's body.

Once the device 10 is releasably connected to the bone anchor 100 as illustrated in FIG. 3A, the device 10 may provide a percutaneous pathway between a skin incision and the bone anchor 100 that facilitates delivery of instruments, spinal connection elements, and/or components of the bone anchor, such as the closure mechanism, to the bone anchor 100. In the illustrated exemplary embodiment, for example, the lumen 24 of the inner tube 12 provides a pathway to the receiving member 108 of the bone anchor 100, that may allow a closure mechanism, such as a set screw, to be delivered to the receiving member 108 of the bone anchor and/or may allow a screw driver or the like to be advanced into engagement with the head 104 of the bone anchor 102. Moreover, in the illustrated exemplary embodiment, the slots 60 of the inner tube and the slots 62 of the outer tube 14 may be aligned with the recess 114 provided in the receiving member 108. Alignment of the slots 60 and 62 with the recess 114 facilitates the delivery of a spinal connection element to the bone anchor 100, as described below. Further exemplary methods and devices for delivering a spinal connection element to a bone anchor are described in U.S. Patent Application Publication No. 2005/0131421 and U.S. Patent Application Publication No. 2005/0131422, each of which are incorporated herein by reference.

Referring to FIGS. 4-7B, an exemplary instrument 150 for adjusting the locking member 90 relative to the inner tube 12 and for adjusting the inner tube 12 relative to the outer tube 14 is illustrated. The exemplary instrument 150 includes an inner sleeve 152 and an outer sleeve 154 positioned about at least a portion of the inner sleeve 152 and coaxial disposed with respect to the inner sleeve 152. The inner sleeve 152 may be axially adjustable relative to the outer sleeve 154 or may be fixed relative to the outer sleeve 154, as in the exemplary embodiment. The outer sleeve 154 may be rotationally adjustable relative to the inner sleeve 152, as in the exemplary embodiment, or may be fixed relative to the inner sleeve 152 such that the outer sleeve 154 and inner sleeve 152 rotate together. The distal end 156 of the outer sleeve 154 may include one or more drive features 158 for engagement with the locking member 90 to adjust the locking member 90 within the outer tube 14 into and out of engagement with the inner tube 12. In the exemplary embodiment, the distal end 160 of the inner sleeve 152 extends from the distal end 156 of the outer sleeve 154 and has one or more projections 162 engageable with an instrument engagement feature provided on the inner tube 12 of the device 10. The instrument engagement feature in the exemplary embodiment is an annular groove 164 provided within the lumen 24 of the inner tube 12. Alternatively, the instrument engagement feature may be one or more slots, openings, projections, or other known structures for engaging an instrument to another instrument or to an implant. The distal end 160 of the inner sleeve 152 of the instrument 150 may be a pair of spaced apart prongs 166A and 166B, each prong 166A,B may include a projection 162 for engagement with the instrument engagement feature, e.g., the annular groove 164, of the inner tube 12. The instrument 150 may further include a central shaft 168 positionable coaxially within the inner sleeve 152 and adjustable with respect to the inner sleeve 152. Distal advancement of the central shaft 168 relative to the inner sleeve 152 may cause radial deployment of the prongs 166A and 166B, and the respective projections 162, from a parallel position to a non-parallel position in which the prongs 166A and 166B are spaced further apart from one another.

Referring to FIGS. 5A-7B, an exemplary method of operation of the exemplary instrument 150 is illustrated. FIGS. 5A and 5B illustrate engagement of the instrument 150 with the locking member 90 of the device 10. The distal end 156 of the outer sleeve 154 is positioned within the lumen 34 of the outer tube 14 and advanced distally until the drive features 158 engage the drive features provided on the locking member 90. The outer sleeve 154 of the instrument 150 may be rotated with respect to the outer tube 14 and the inner tube 12 to move the locking member 90 distally into engagement with the proximal end 20 of the inner tube 12, as illustrated in FIGS. 6A and 6B. During advancement of the locking member 90, the projections 162 of the inner sleeve 152 are axially aligned with the annular groove 164 of the inner tube 12, as illustrated in FIGS. 6A and 6B. The instrument 150 may then be removed to permit delivery of a spinal connection element or other implants or instruments to the bone anchor 100.

To adjust the inner tube 12 relative to the outer tube 14 to facilitate removal of the device 10 from the bone anchor 100 after, for example, spinal connection element delivery, the instrument 150 may be reinserted into the device 10. The central shaft 168 of the instrument 150 may be advanced distally relative to the inner sleeve 152 to cause radial deployment of the prongs 166A and 166B, and the respective projections 162, from a parallel position (FIGS. 6A and 6B) to a non-parallel position in which the prongs 166A and 166B are spaced further apart from one another and the projections 162 are positioned within the annular groove 164, as illustrated in FIGS. 6C and 6D. The outer sleeve 154 of the instrument 150 may be rotated to adjust the locking member 90 proximally away from the proximal end 20 of the inner tube 12. During adjustment of the locking member 90 proximally, the inner sleeve 152 of the instrument 150 adjusts the inner tube 12 of the device 10 proximally, against the spring force provided by spring 50, such that the distal end 22 of the inner tube 12 is spaced apart from the proximal end of the receiving member 108 of the bone anchor 100 (FIGS. 7A and 7B), thereby facilitating removal of the device 10 from the bone anchor 100. Alternatively, adjustment of the locking member 90 proximally and adjustment of the inner tube 12 may occur in discrete separate steps.

Figure 8:
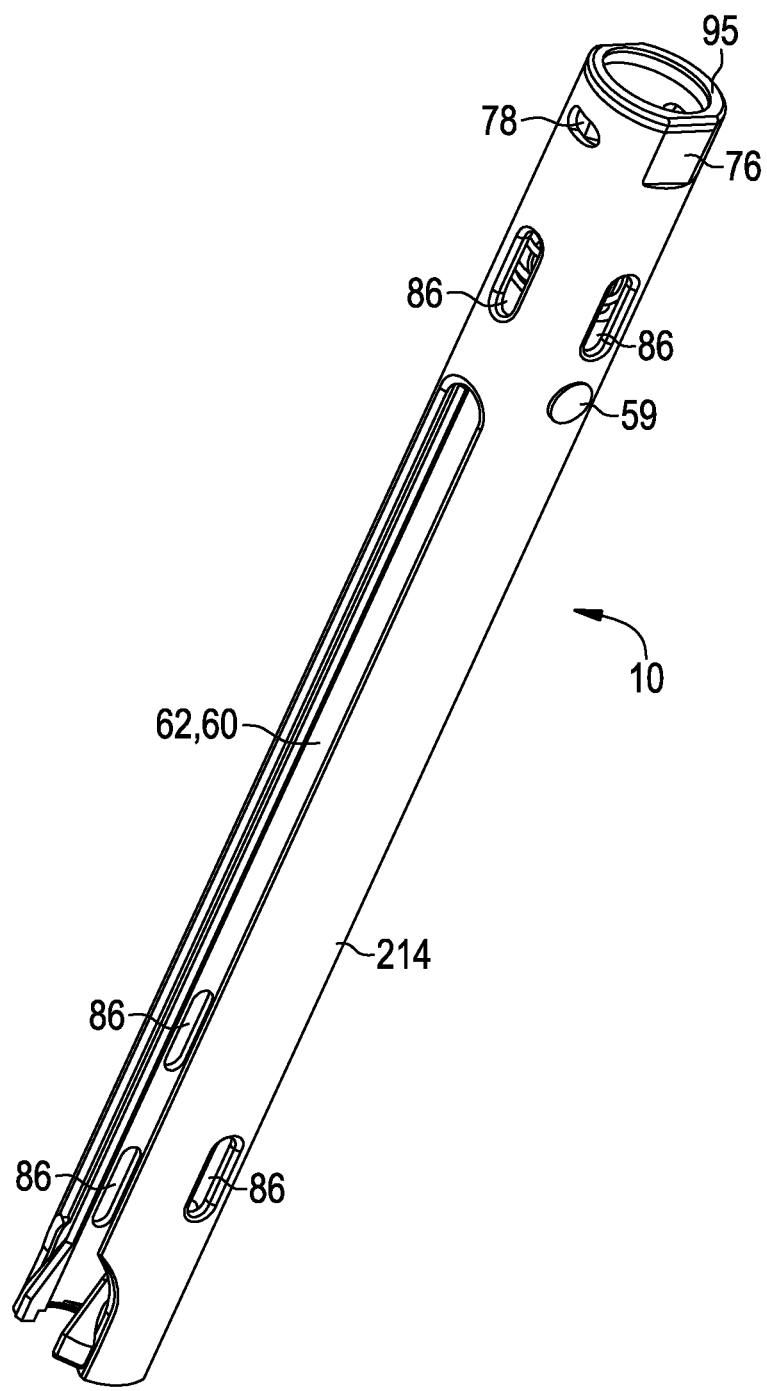
FIG. 8 is a perspective view of another exemplary embodiment of a device for delivery of a spinal connection element, such as a spinal rod, to a bone anchor.
Figure 9:
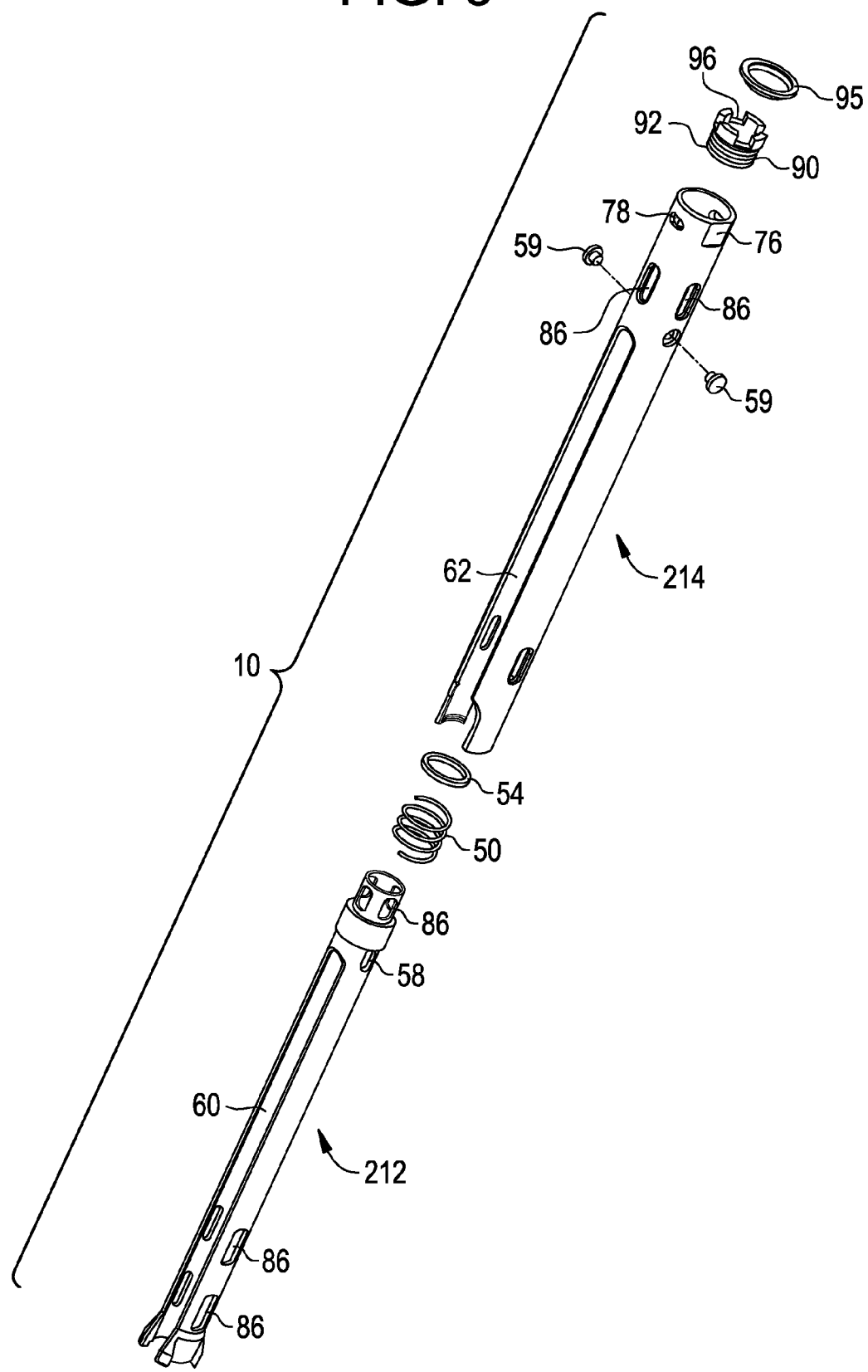
FIG. 9 is an exploded view of the device of FIG. 8.

FIGS. 8 and 9 illustrate another embodiment of an exemplary device 210 that is analogous in construction in operation to the device 10 illustrated above. In the exemplary embodiment, the length of the inner tube 212 of the device 210 is approximate the length of the outer tube 214 of the device 210. The length of the slots 60 and 62 is selected to span at least from the skin incision to the distal end of the inner tube 212 and the outer tube 214, respectively. In the exemplary embodiment, the slots 60 and 62 may be accessible from outside of the patient. The outer tube 214 of the device 210 includes a pair of diametrically opposed flat surfaces 76 and a pair of diametrically opposed openings, in the form of slots 78, to facilitate engagement of the outer tube 214 with an instrument. In the exemplary embodiment, in which the locking member 90 is positioned within the lumen 34 of the outer tube 14, a cap 95 may be positioned at the proximal end of the outer tube 214 to inhibit removal of the locking member 90 from the within the outer tube 214.

Figure 17A:
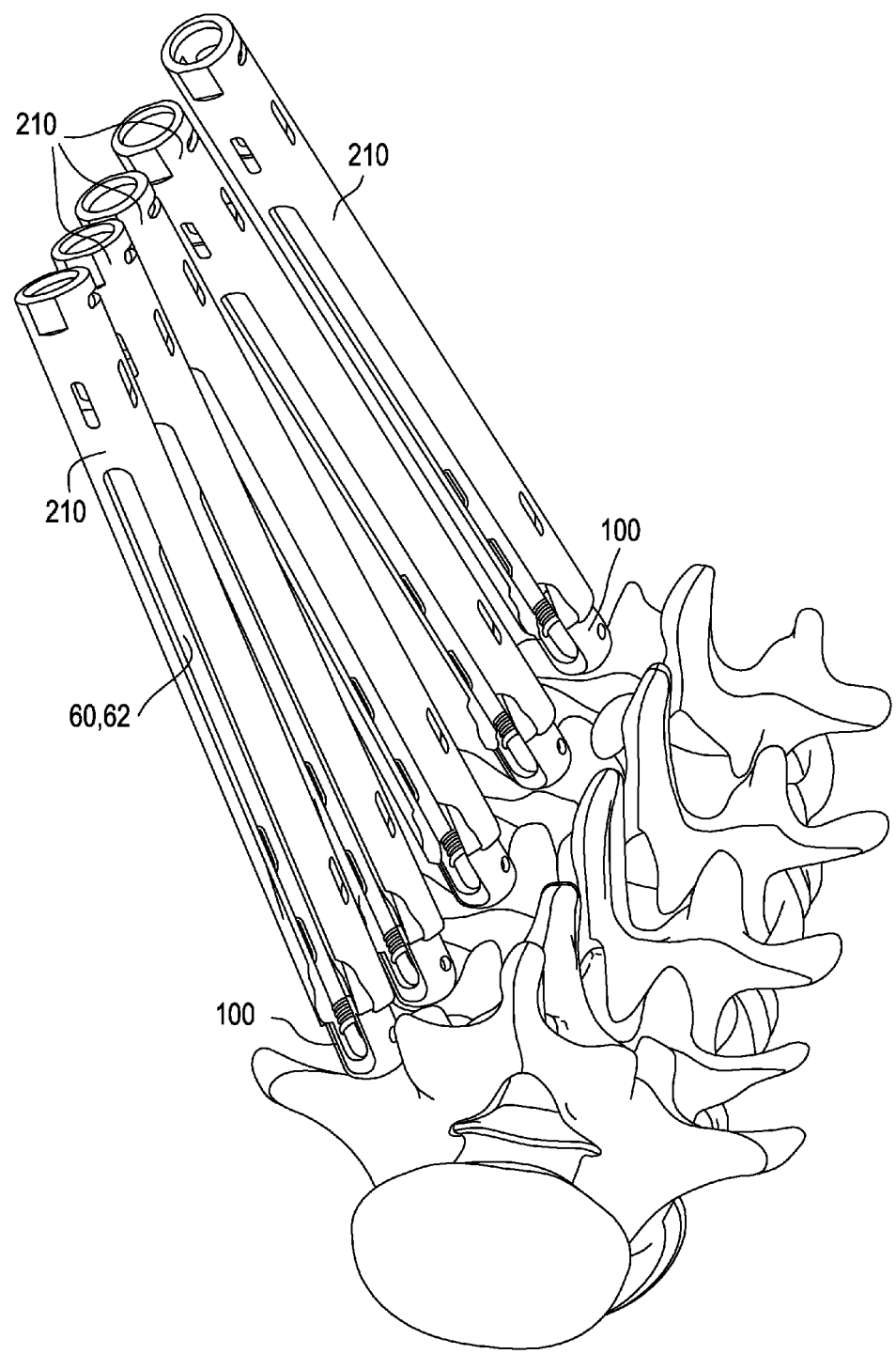
FIGS. 17A-D are perspective views of a plurality of devices of FIG. 8, illustrating delivery of a spinal connection element to a plurality of bone anchors each implanted in a vertebra of the spine.
Figure 17B:
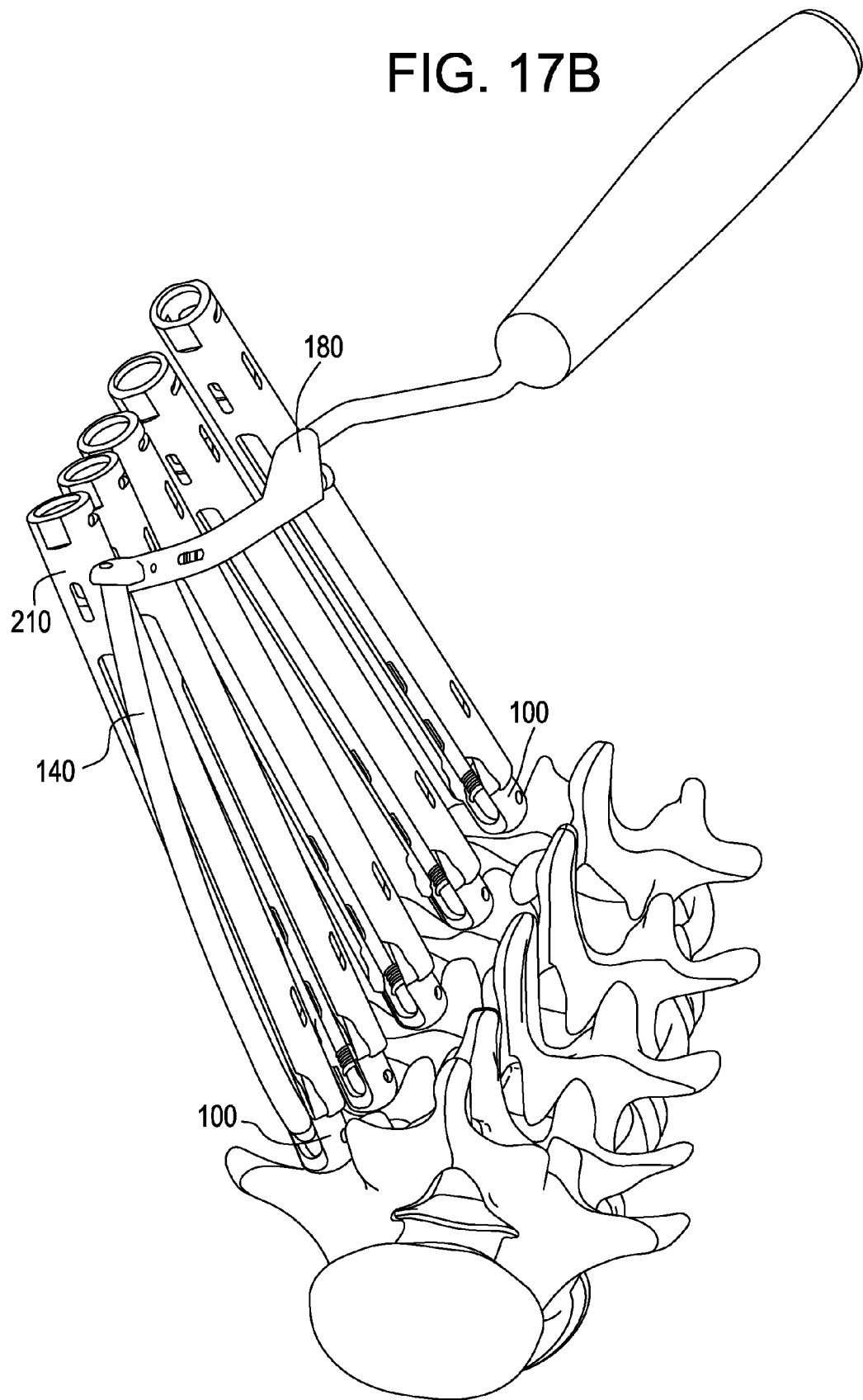
Figure 17C:
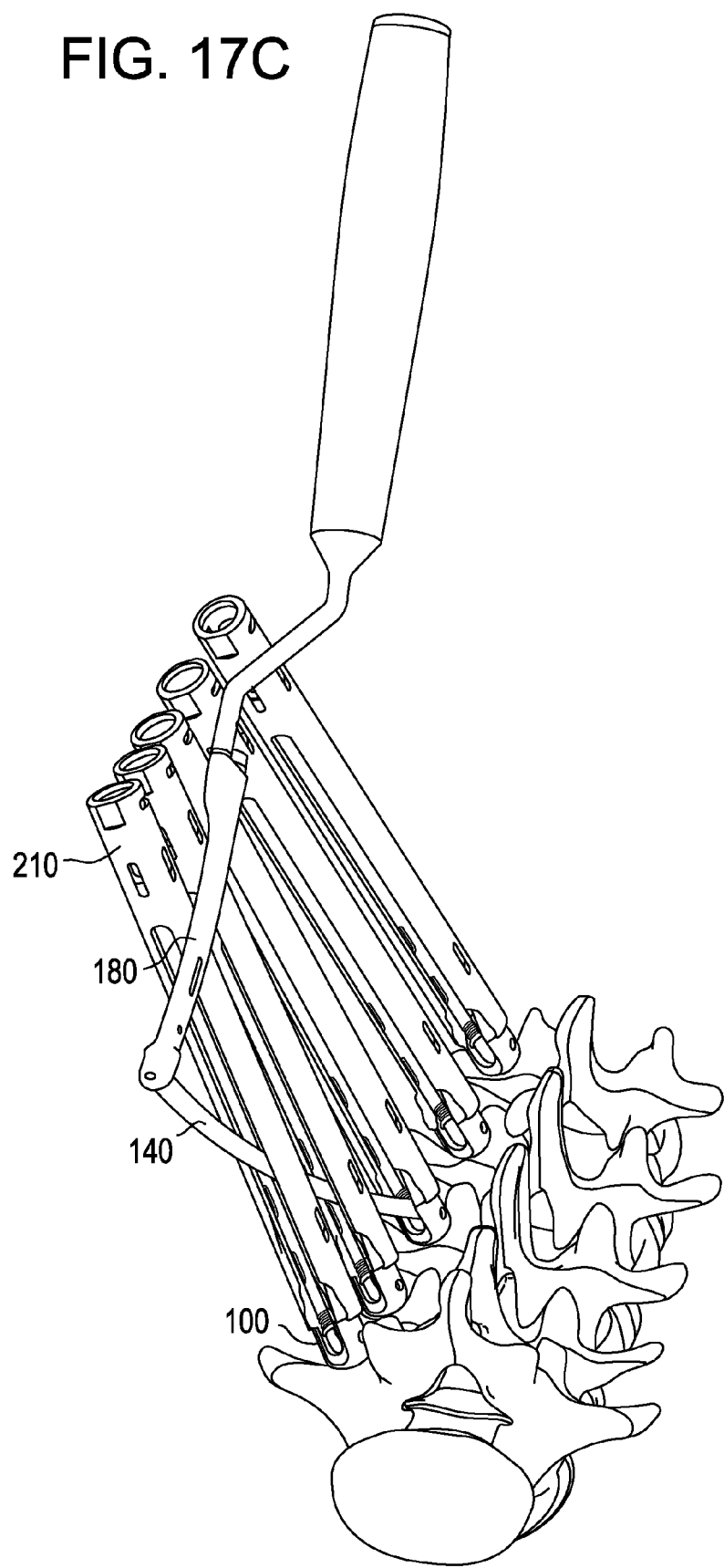
Figure 17D:
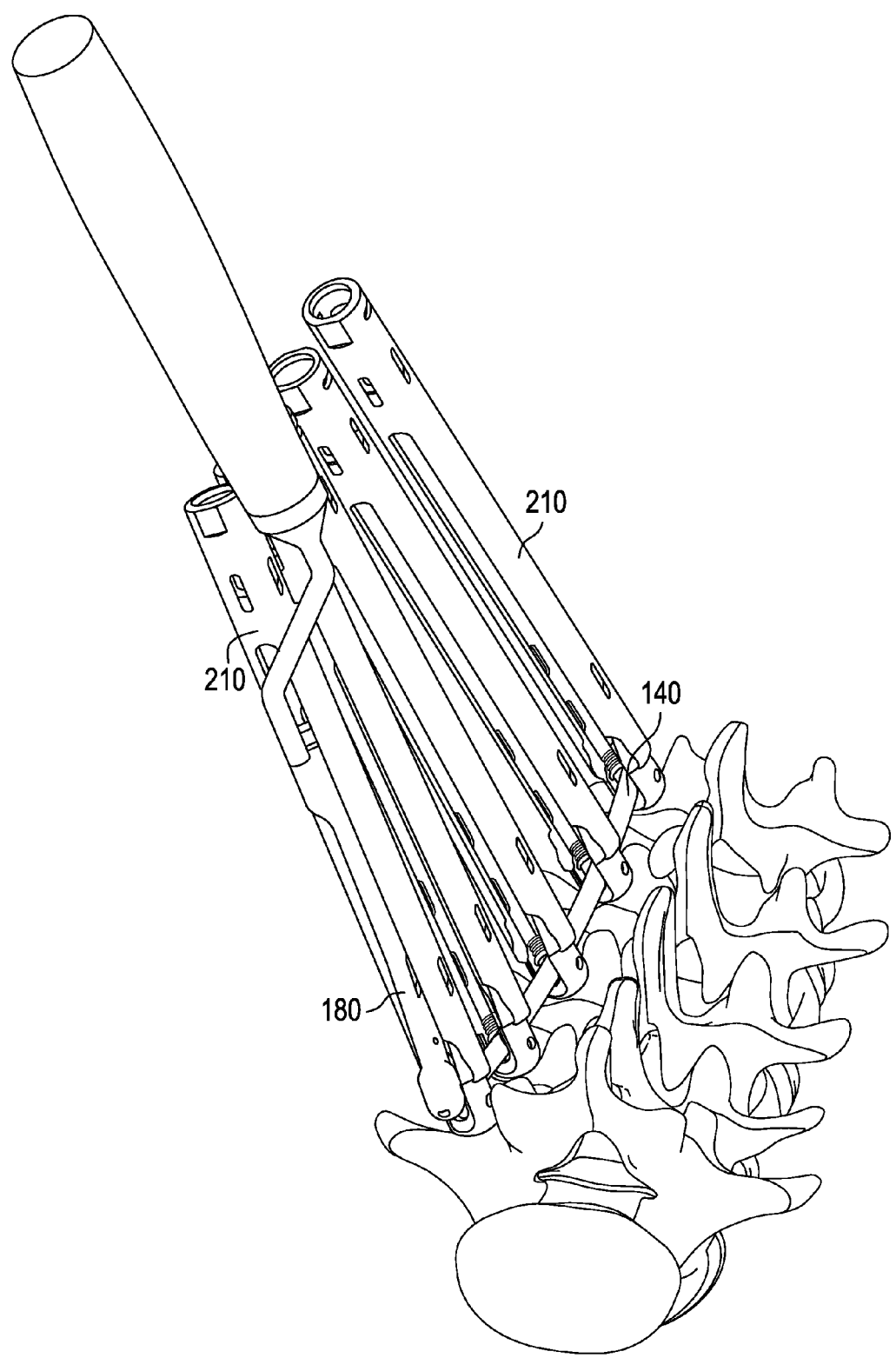

FIGS. 17A-17D illustrate an exemplary methods of delivering a spinal connection element, e.g., a spinal rod 140, to one or more bone anchors 100 using the exemplary device 210. The exemplary method described herein is a multi-level procedure in which a bone anchor 100 is implanted in a plurality, five, adjacent vertebrae and a spinal rod 140 is delivered to the each of the bone anchors 100 to connect the bone anchors and provide stability to the vertebrae until fusion of the vertebrae occur. The exemplary method may be employed to instrument any number of spine levels, from a single level (two vertebrae) to multiple levels (three or more vertebrae). In the exemplary method, each bone anchor 100 may be connected to a device, such as device 10 or device 210, in the manner described above. The bone anchors 100 may be implanted in a vertebra through a single open incision or, more preferably, each bone anchor 100 and its respective device 210 are delivered through a separate minimally invasive stab incision in the patient to proximate a vertebra of the patient, as illustrated in FIG. 17A. After anchoring at least one bone anchor 100 in a vertebra, a spinal rod 140 may be advanced through the stab incision used for the bone anchor 100 and through at least a portion of the device 210 to the bone anchor 100. The spinal rod 100 may be advance to the bone anchor 100 by pivoting the spinal rod 140 sub-dermally (i.e., beneath the skin) from a first orientation to a second orientation substantially parallel to the axis of the spine of the patient, as illustrated in FIGS. 17B-17D. A rod delivery instrument 180 may be employed to manipulate the spinal rod 140. In the first orientation, the spinal rod 140 may be oriented substantially parallel to or at an angle to the device 210. During pivoting of the spinal rod, 140, the leading end of the spinal rod 140 and at least a portion of the length of the spinal rod 140 may pass through the slots 60 and 62 of one or more of the devices 210. The spinal rod 140 may be inserted through the same incision as the device 210 and the bone anchor 100 either through the lumen of the inner tube 212 of the device 210 or external to the device 210 (but still through the same incision of the device 210), as illustrated in FIG. 17B. Once the spinal rod 140 is positioned proximate each bone anchor, the spinal rod 140 may be connected to each of the bone anchors by a closure mechanism, which may delivered to the bone anchor through the device 10. Each device 210 may then be removed its respective bone anchor 100.

Figure 10:
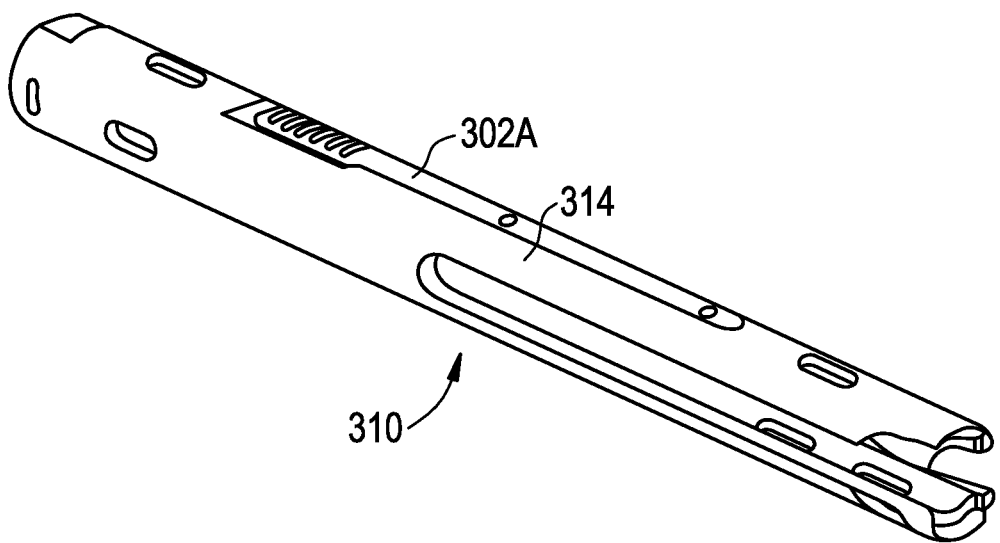
FIG. 10 is a perspective view of another exemplary embodiment of a device for delivery of a spinal connection element, such as a spinal rod, to a bone anchor.
Figure 11:
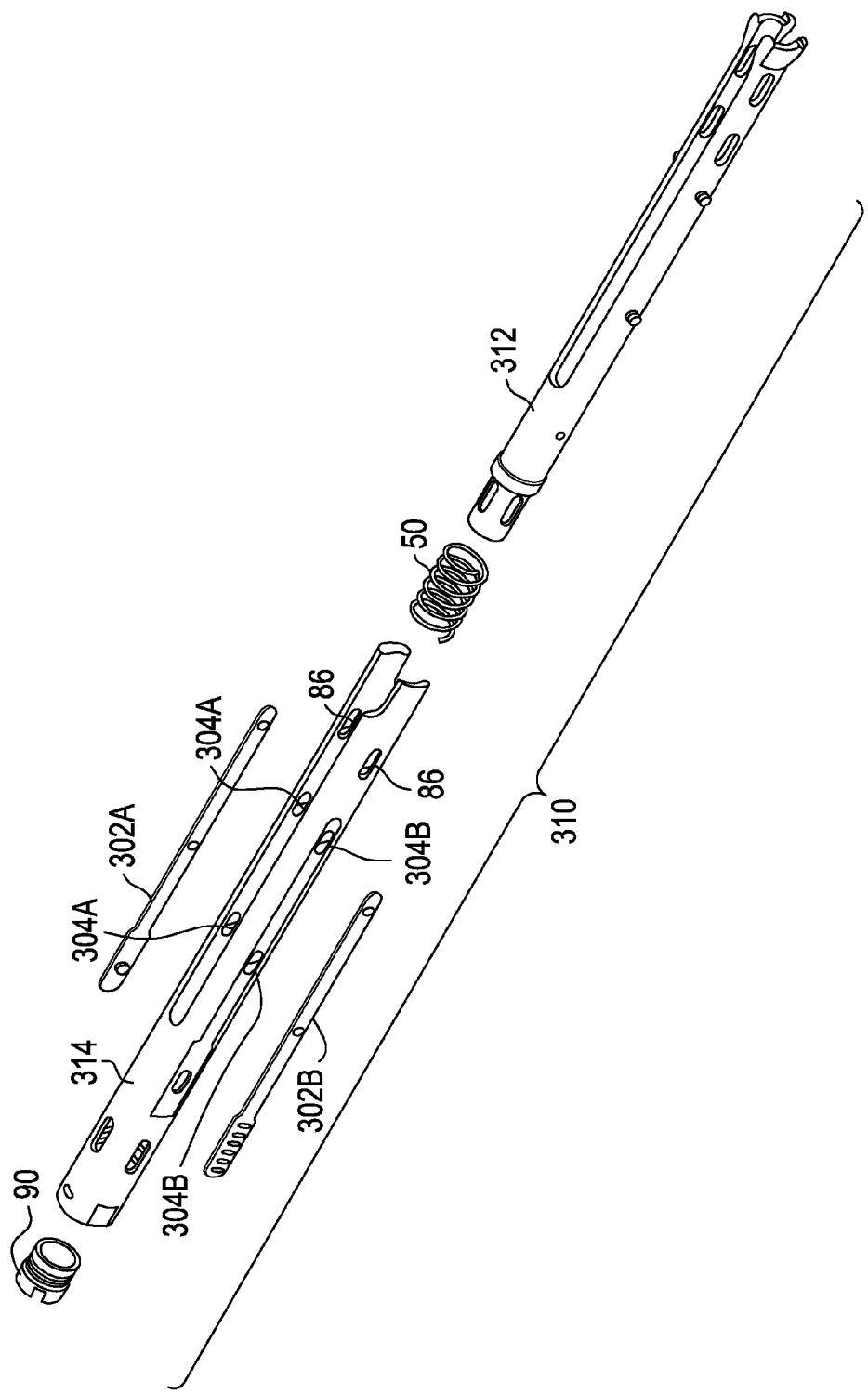
FIG. 11 is an exploded view of the device of FIG. 10.

FIGS. 10 and 11 illustrate another embodiment of an exemplary device 310 that is analogous in construction in operation to the device 10 illustrated above. The device 310 includes a first sliding member 302A connected through one or more openings 304A in the outer tube 314 to the inner tube 312 to permit adjustment of the inner tube 312 relative to the outer tube 314. The device 310 may further include additional sliding members, such as a second sliding member 302B connected through one or more second openings 304B in the outer tube 314 to the inner tube 312. The second sliding member 302B may be positioned diametrically opposite the first sliding member 302B or at other suitable locations. Proximal adjustment of the sliding members 302A and 30B cause the inner tube to be adjusted proximally relative to the outer tube 314, in opposition to the spring force provided by the spring 50, to facilitate release of the device 310 from a bone anchor without the need for a separate instrument, such as instrument 150 described above.

Figure 12:
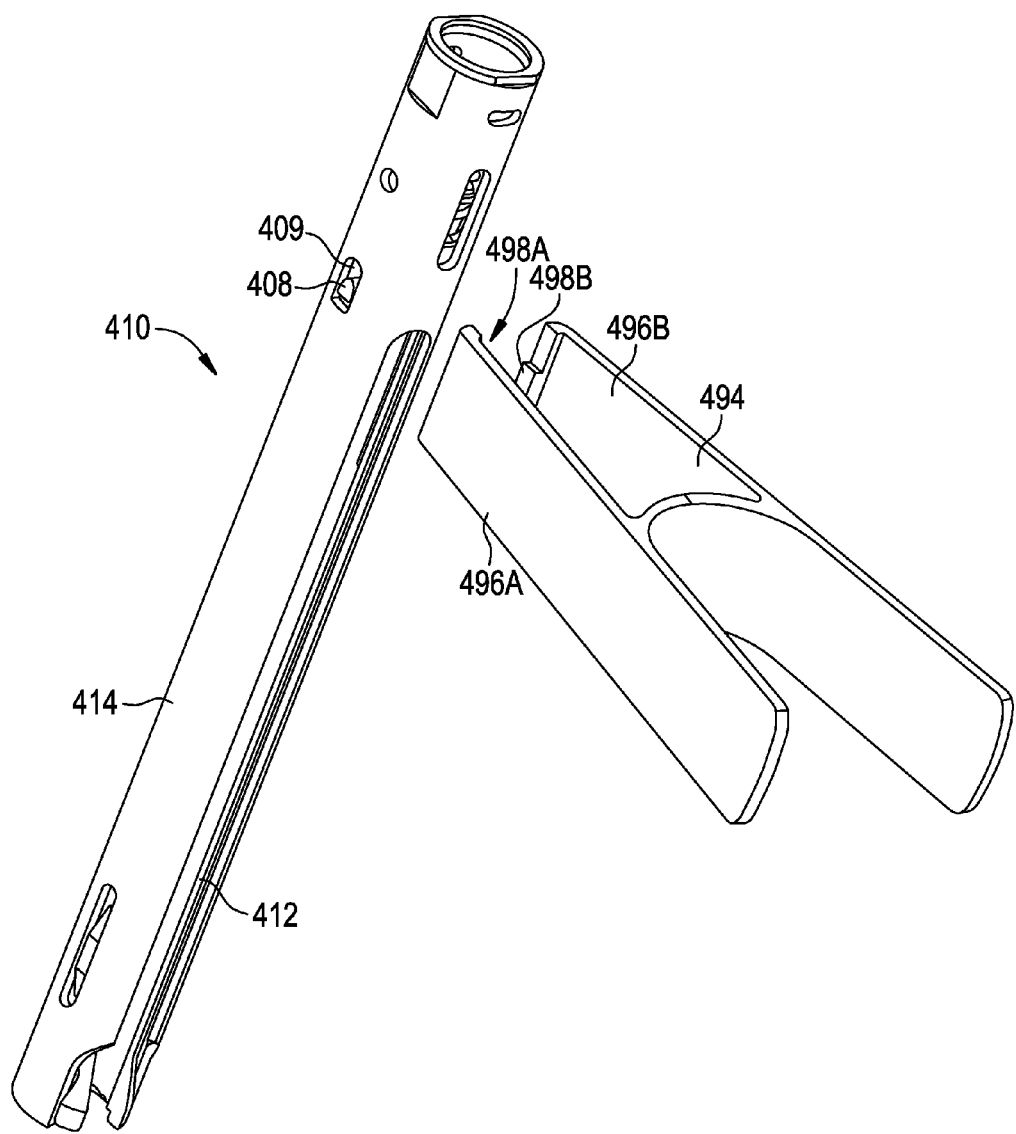
FIG. 12 is a perspective view of another exemplary embodiment of a device for delivery of a spinal connection element, such as a spinal rod, to a bone anchor and of an instrument for removing the inner tube of the device from the outer tube of the device.
Figure 13:
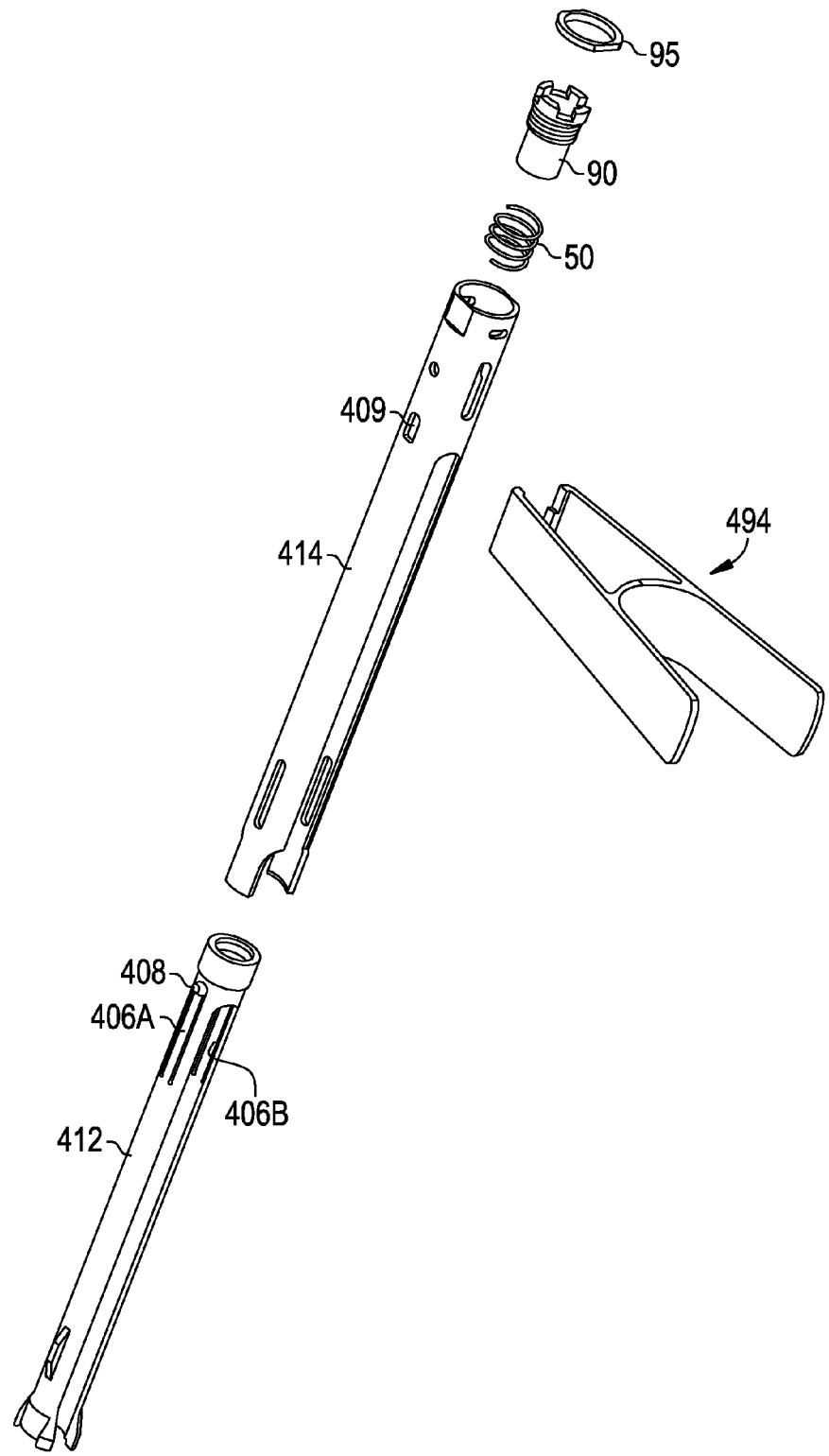
FIG. 13 is an exploded view of the device of FIG. 12.
Figure 14:
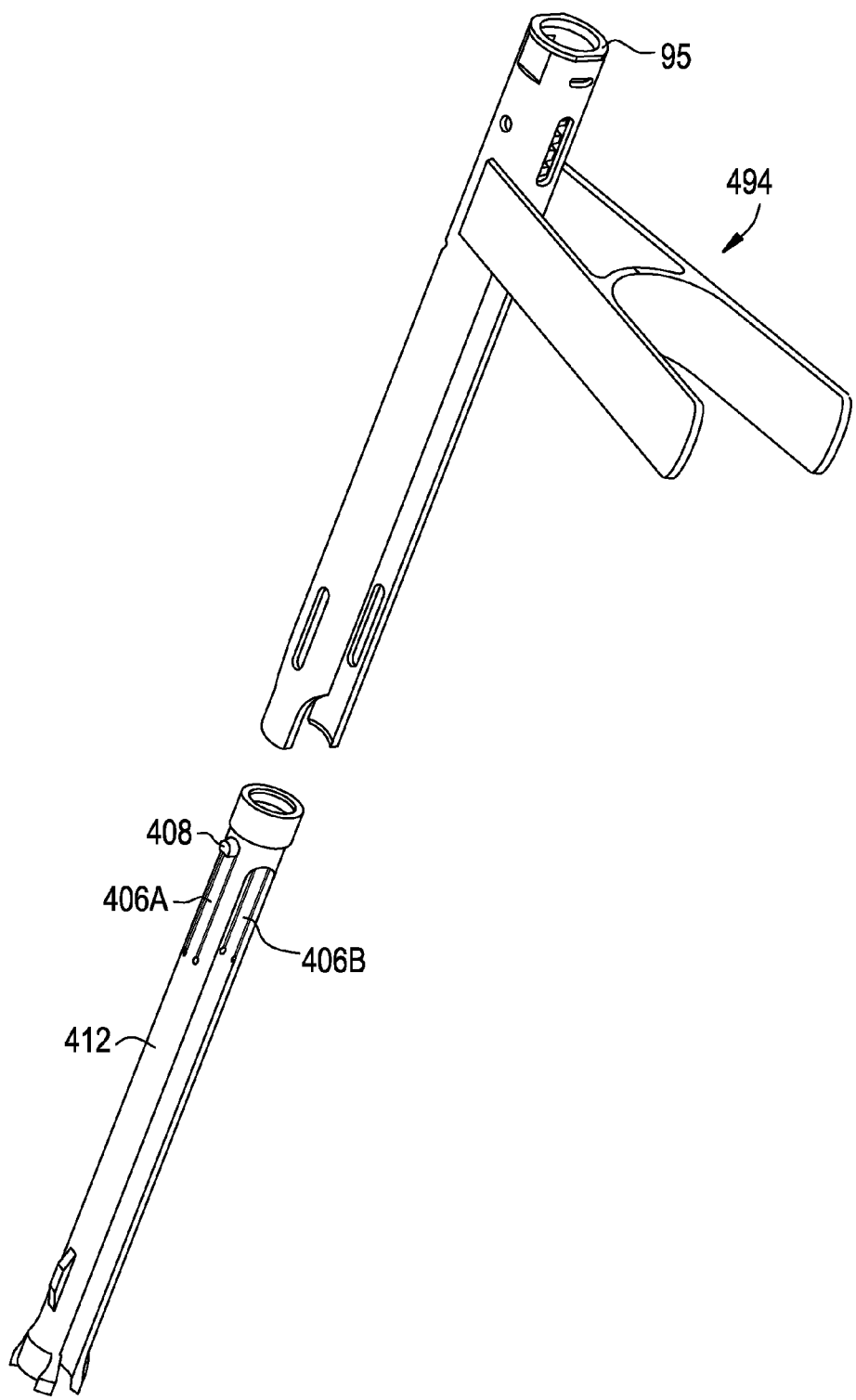
FIG. 14 is a perspective view of the device of FIG. 12, illustrating removal of the inner tube of the device from the outer tube of the device.

FIGS. 12-14 illustrate another embodiment of an exemplary device 410 that is analogous in construction in operation to the device 10 illustrated above. In the exemplary device 410, the inner tube 412 is removable and replaceable from the outer tube 414 to facilitate cleaning of the inner tube 412. For example, the inner tube 414 may include a pair of adjustable prongs 406A and 406B each of which is connected to the inner tube 412 at a first end. Each prong 406A and 406 B may have a free end opposite the first end having a projection 408 positioned thereon. The prongs 406A and 406B may be biased to a first position in which the projection 408 is received in an opening 409 in the outer tube 414 and may be adjustable to a second position in which the projection 408 is removed from the opening 408 to facilitate removal of the inner tube 412 from the outer tube 414 for cleaning. An instrument 494 may be provided to adjust the prongs to the second position. The instrument 494 may include a pair of jaw members 496A and 496B having projections 498A and 498B sized and shaped to fit within the openings 409 to engage the projections 408 on the prongs 406A and 406B and adjust the prongs 406A and 406B to the second position.

Figure 15:
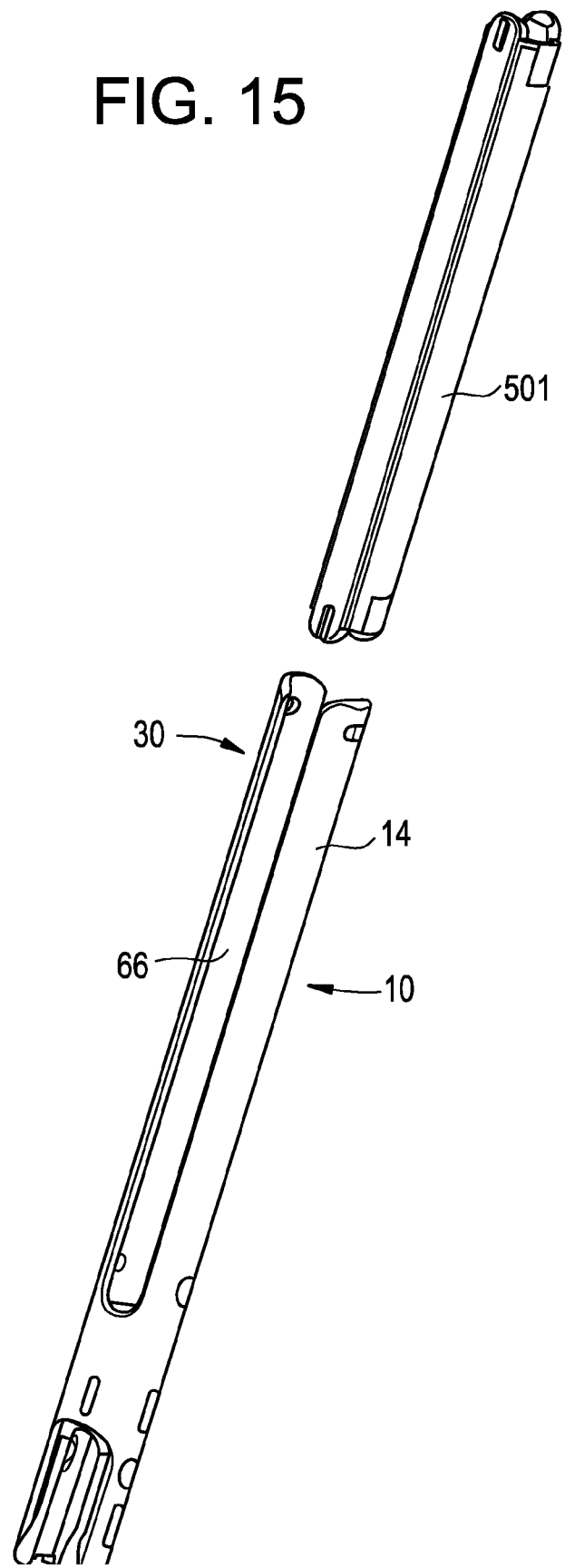
FIG. 15 is a perspective view of the device of FIG. 1 and a reinforcing instrument positionable within the device.
Figure 16:
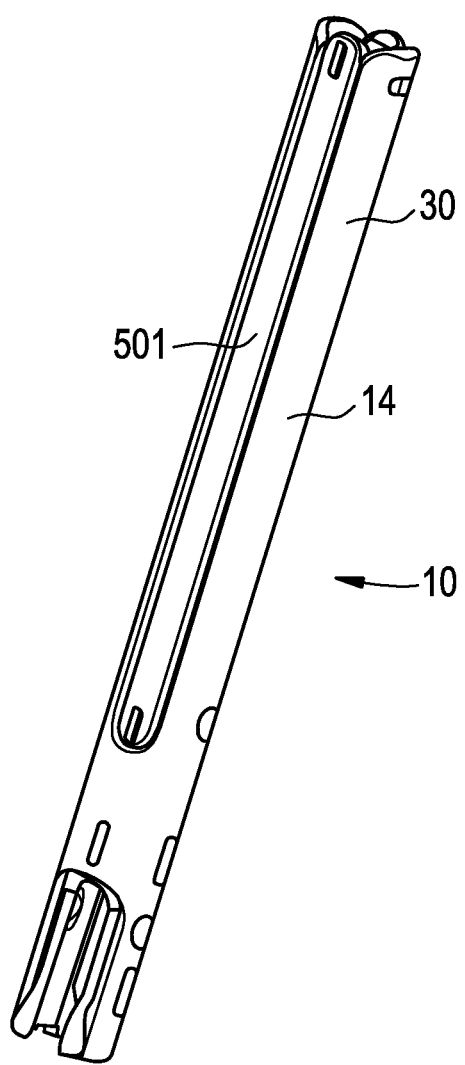
FIG. 16 is a perspective view of the reinforcing instrument of FIG. 15 positioned within the device of FIG. 1.

FIGS. 15 and 16 illustrate a reinforcing instrument 501 that may be positioned within the device 10 or the other devices described herein. The reinforcing instrument 501 is generally cylindrical in shape and, in the exemplary embodiment, is sized to fit within the lumen of the outer tube 14 of the device 10 to provide stability to the outer tube 14 and to inhibit collapse of the proximal end 30 of the outer tube 14 during manipulation of the device 10. For example, the instrument 501 may have a cross-sectional extent, e.g., a diameter, approximately equal to the cross-section extent of the outer tube 14. The length of the reinforcing instrument 501 may be approximately equal to the length of the proximal slots 66.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A device for delivery of a spinal rod to a bone anchor, the device comprising:
    an inner tube having a proximal end, a distal end, and a lumen extending between the proximal end and the distal end, the inner tube having a first slot formed therein, the first slot opening at the distal end of the inner tube and extending a first slot length toward the proximal end of the inner tube;
    an outer tube disposed about at least a portion of the inner tube, the outer tube having a proximal end, a distal end, and a lumen extending between the proximal end and the distal end, the outer tube being sized to span from at least a skin incision in a patient to a predetermined site proximate the spine of the patient, the outer tube having an internal thread provided within the lumen of the outer tube, the outer tube having a second slot formed therein, the second slot opening at the distal end of the outer tube and extending a second slot length toward the proximal end of the outer tube, the distal end of the outer tube being adapted to releasably engage a bone anchor, the inner tube being adjustable relative to the outer tube along the longitudinal axis of the outer tube between a first position and a second position in which the distal end of the inner tube contacts the bone anchor, the first slot length and the second slot length sized to span at least from a skin incision to the distal ends of the inner tube and the outer tube, respectively, such that the first slot and the second slot may be accessible from outside of the patient when the device is in use in surgery;
    a spring positioned within the outer tube and interposed between the inner tube and the outer tube, the spring biasing the inner tube distally; and
    a cylindrical locking member positioned within the lumen of the outer tube, the locking member having a central lumen and an external thread for engagement with the internal thread within the lumen of the outer tube, the locking member being adjustable relative to the outer tube along the longitudinal axis of the outer tube between a proximal position in which the locking member is spaced apart from the inner tube to permit proximal axial movement of the inner tube relative to the outer tube and a distal position in which the locking member abuts the proximal end of the inner tube to inhibit proximal axial motion of the inner tube relative to the outer tube, the central lumen of the locking member and the lumen of the inner tube being sized to pass a closure mechanism for a bone anchor therethough.

2. The device of claim 1, wherein the spring is interposed between the inner tube and a shoulder provided on an inner surface of the outer tube.

3. The device of claim 1, wherein the spring is positioned about a portion of the inner tube.

4. The device of claim 1, further comprising a washer interposed between the spring and a shoulder provided on an inner surface of the outer tube.

5. The device of claim 1, wherein the inner tube includes a shoulder on an outer surface of the inner tube, the outer tube including a shoulder on an inner surface of the outer tube, a distal end of the spring abutting the shoulder on the inner tube and a proximal end of the spring abutting a washer interposed between the spring and the shoulder on the outer tube.

6. The device of claim 1, wherein the distal end of the outer tube includes a plurality of instrument engagement features.

7. The device of claim 6, wherein the plurality of instrument engagement features are a plurality of flat surfaces provided at spaced apart locations on an outer surface of the outer tube.

8. The device of claim 6, wherein the plurality of instrument engagement features are a plurality of openings provided at spaced apart locations on an outer surface of the outer tube.

9. The device of claim 1, further comprising a cap positioned on the proximal end of the outer tube to inhibit removal of the locking member from within the outer tube.

10. The device of claim 1, wherein the distal end of the outer tube includes a pair of opposed tabs, each tab including an angled surface to facilitate positioning of the tabs about a bone anchor.

11. The device of claim 10, wherein each tab includes a radially inward projection for engaging a connection feature on a bone anchor.

12. The device of claim 11, wherein the spring biases the distal end of the inner tube into abutment with a proximal surface of the radially inward projection of each tab prior to connection with a bone anchor.

13. The device of claim 1, wherein the inner tube includes a retaining slot oriented along the longitudinal axis of the inner tube, the retaining slot receiving a projection from an inner surface of the outer tube.

14. The device of claim 1, wherein the inner tube is removable and replaceable from the outer tube to facilitate cleaning of the inner tube.

15. A medical device comprising:
a device for delivery of a spinal rod to a bone anchor comprising
an inner tube having a first slot formed therein, the first slot having an opening at a distal end of the inner tube and extending a first slot length toward a proximal end of the inner tube,
an outer tube coaxially disposed about at least a portion of the inner tube, the outer tube being sized to span from at least a skin incision in a patient to a predetermined site proximate the spine of the patient, the outer tube having an internal thread provided within a lumen of the outer tube, the outer tube having a second slot formed therein aligned with the first slot, the second slot having an opening at a distal end of the outer tube and extending a second slot length toward a proximal end of the outer tube, the first slot length and the second slot length sized to span at least from a skin incision to the distal ends of the inner tube and the outer tube, respectively, such that the first slot and the second slot may be accessible from outside of the patient when the device is in use in surgery,
a spring positioned within the outer tube and interposed between the inner tube and the outer tube, the spring biasing the inner tube distally, and
a cylindrical locking member positioned within the lumen of the outer tube, the locking member having a central lumen and an external thread for engagement with the internal thread within the lumen of the outer tube, the locking member being adjustable relative to the outer tube along the longitudinal axis of the outer tube between a proximal position in which the locking member is spaced apart from the inner tube to permit proximal axial movement of the inner tube relative to the outer tube and a distal position in which the locking member abuts the proximal end of the inner tube to inhibit proximal axial motion of the inner tube relative to the outer tube; and
a bone anchor assembly comprising a bone anchor having a proximal head and a distal bone engaging portion, and a receiving member having a proximal end having a recess for receiving a spinal rod, the proximal head of the bone anchor positioned in the receiving member and the distal bone engaging portion extending from the receiving member, wherein the distal end of the outer tube is releasably engaged to the receiving member and the first and second slots are aligned with the recess in the receiving member when the outer tube is releasably engaged to the receiving member,
wherein the central lumen of the locking member and a lumen of the inner tube are sized to pass a closure mechanism for the bone anchor assembly therethrough.

16. A medical device comprising:
a device for delivery of a spinal rod to a bone anchor comprising
an inner tube having a proximal end, a distal end, and a lumen extending between the proximal end and the distal end, the inner tube having a first slot formed therein, the first slot having an opening at a distal end of the inner tube and extending a first slot length toward a proximal end of the inner tube,
an outer tube disposed about at least a portion of the inner tube, the outer tube having a proximal end, a distal end, and a lumen extending between the proximal end and the distal end; the outer tube being sized to span from at least a skin incision in a patient to a predetermined site proximate the spine of the patient, the outer tube having an internal thread provided within the lumen of the outer tube, the outer tube having a second slot formed therein aligned with the first slot, the second slot having an opening at the distal end of the outer tube and extending a second slot length toward the proximal end of the outer tube, the first slot length and the second slot length sized to span at least from a skin incision to the distal ends of the inner tube and the outer tube, respectively, such that the first slot and the second slot may be accessible from outside of the patient when the device is in use in surgery,
a spring positioned within the outer tube and interposed between the inner tube and the outer tube, the spring biasing the inner tube distally, and
a cylindrical locking member positioned within the lumen of the outer tube, the locking member having a central lumen and an external thread for engagement with the internal thread within the lumen of the outer tube, the locking member being adjustable relative to the outer tube along the longitudinal axis of the outer tube between a proximal position in which the locking member is spaced apart from the inner tube to permit proximal axial movement of the inner tube relative to the outer tube and a distal position in which the locking member abuts the proximal end of the inner tube to inhibit proximal axial motion of the inner tube relative to the outer tube, and a bone anchor assembly comprising:
- a bone anchor having a proximal head and a distal bone engaging portion; and
- a receiving member coupled to the bone anchor, the receiving member having a proximal end, a distal end and a recess for receiving a spinal rod, the proximal end of the receiving member having a pair of arcuate grooves formed on an exterior surface thereof, wherein the distal end of the outer tube includes a pair of opposed tabs, each tab having a radially inward projection that is sized and shaped to seat within one of the arcuate grooves formed in the receiving member of a bone anchor, wherein the central lumen of the locking member and the lumen of the inner tube are sized to pass a closure mechanism for the bone anchor assembly therethrough.

\* \* \* \* \*